US012606628B2

(12) United States Patent
    Singh Sidhu

(10) Patent No.:  US 12,606,628 B2
(45) Date of Patent:  Apr. 21, 2026

(54) ANTIBODIES TARGETING INTEGRIN BETA-2

(71) Applicant: Sachdev Singh Sidhu, Toronto (CA)

(72) Inventor: Sachdev Singh Sidhu, Toronto (CA)

( * ) Notice: Subject to any disclaimer, the term of this patent is extended or adjusted under 35 U.S.C. 154(b) by 419 days.

(21) Appl. No.: 18/331,901

(22) Filed: Jun. 8, 2023

(65) Prior Publication Data

US 2024/0101680 A1      Mar. 28, 2024

Related U.S. Application Data

(60) Provisional application No. 63/350,299, filed on Jun. 8, 2022.

(51) Int. Cl.
| | |
|---|---|
| *C07K 16/28* | (2006.01) |
| *C07K 14/725* | (2006.01) |
| *C12N 15/13* | (2006.01) |
| *C12N 15/63* | (2006.01) |

(52) U.S. Cl.
     CPC ...... *C07K 16/2845* (2013.01); *C07K 14/7051* (2013.01); *C07K 2317/31* (2013.01); *C07K 2317/622* (2013.01)

(58) Field of Classification Search
     None
     See application file for complete search history.

(56) References Cited

U.S. PATENT DOCUMENTS

| | | |
|---|---|---|
| 5,817,515 A | 10/1998 | Gallatin et al. |
| 5,985,279 A | 11/1999 | Waldmann et al. |

FOREIGN PATENT DOCUMENTS

EP        0438312 A2     7/1991

OTHER PUBLICATIONS

Caldas et al., "Humanization of the anti-CD18 antibody 6.7: an unexpected effect of a framework residue in binding to antigen". Molecular Immunology, May 2003 (May 2003), vol. 39 (15), pp. 941-952.
CIPO as International Searching Authority, International Search Report and Written Opinion for PCT/CA2023/050791, Jul. 20, 2023.
Huang et al., "Structural and Functional Studies with Antibodies to the integrin B2 Subunit". Journal of Biological Chemistry, Jul. 14, 2000 (Jul. 14, 2000), vol. 275 (28), pp. 21514-21524.

*Primary Examiner* — Christine J Saoud
*Assistant Examiner* — Jon M Lockard
(74) *Attorney, Agent, or Firm* — Own Innovation; James W. Hinton; Sanjeevan Shivakumar

(57)                    ABSTRACT

Provided herein are antibodies that specifically target integrin beta-2 and compositions comprising such antibodies for therapeutic and diagnostic applications. The antibodies comprise an integrin beta-2 binding domain comprising a heavy chain variable region comprising an HCDR1 sequence comprising ISYYYM, an HCDR2 sequence comprising SIS-SSSGYTY; and an HCDR3 sequence comprising GAM; and a light chain variable region comprising an LCDR1 sequence comprising SVSSA, an LCDR2 sequence comprising SASSLYS; and an LCDR3 sequence comprising FSSGSWAPI.

20 Claims, 26 Drawing Sheets
Specification includes a Sequence Listing.

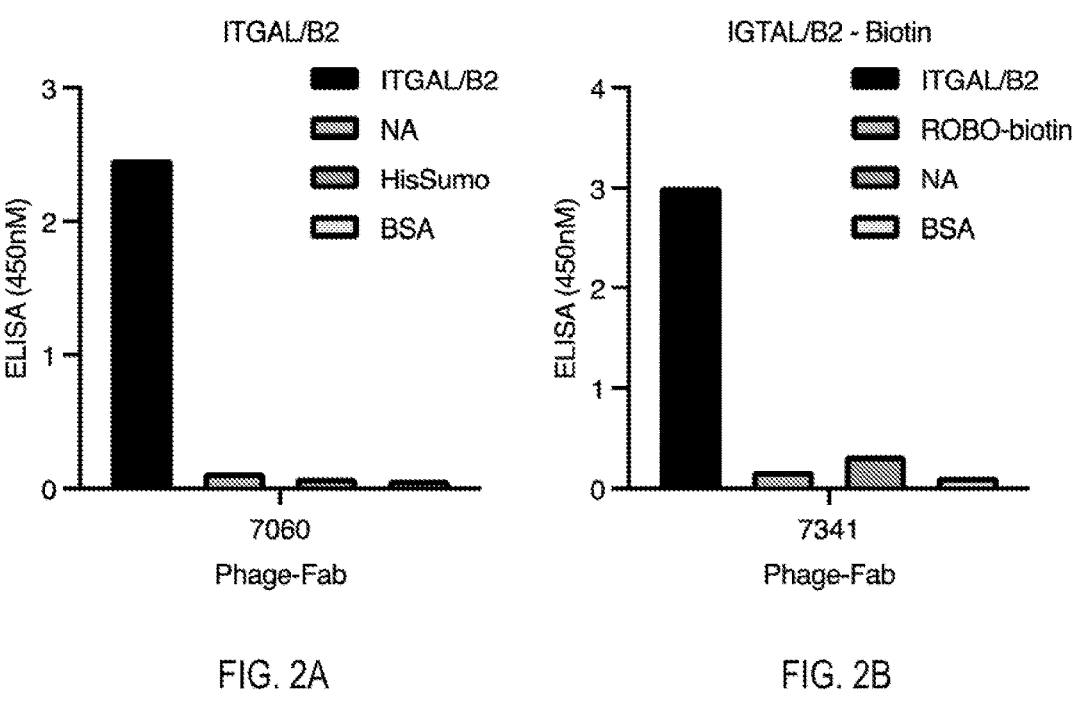
FIG. 2A                   FIG. 2B
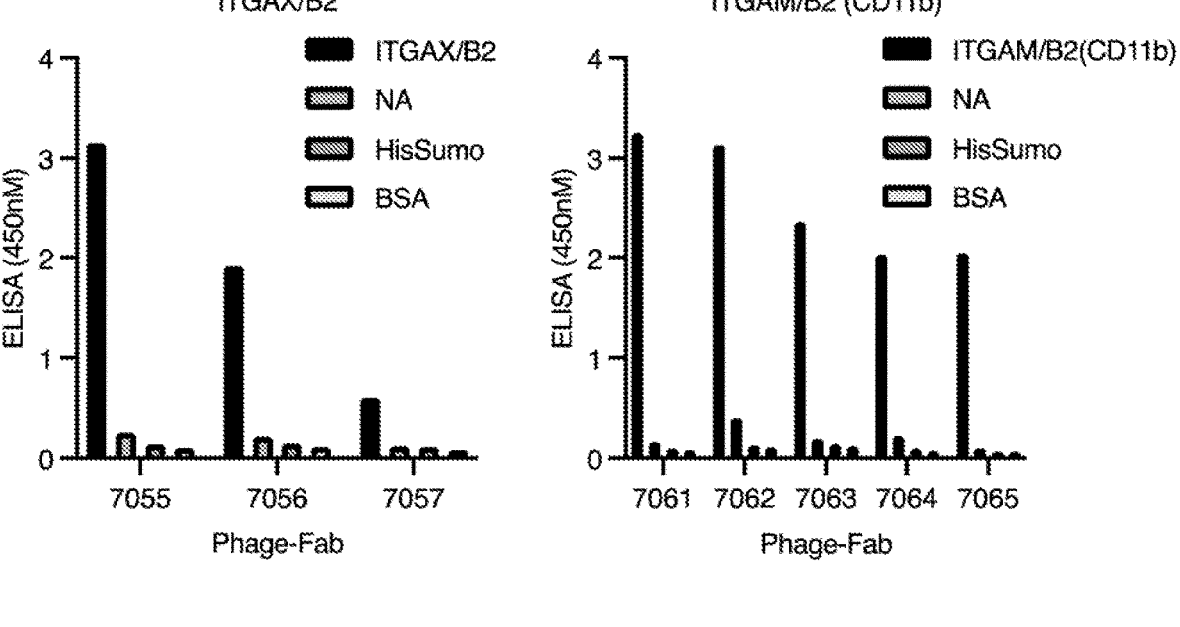
FIG. 2C                   FIG. 2D

| ID | Antigen | LCDR1 | LCDR2 | LCDR3 | HCDR1 | HCDR2 | HCDR3 |
|---|---|---|---|---|---|---|---|
| 7060 | ITGAL/B2 | SVSSA | SASSLYS | YHGSLI | LSYSSM | YIYPSYGYTY | WSPGSGWAF |
| 7341 | ITGAL/B2 | SVSSA | SASSLYS | FYGGYSLI | LSYYYM | SISSYYGYTS | GAL |
| 7061 | ITGAM/B2(CD11b) | SVSSA | SASSLYS | GPVYHLI | FSSSSI | SISSSYGYTY | WYAM |
| 7062 | ITGAM/B2(CD11b) | SVSSA | SASSLYS | YYYAASLF | ISSYSI | SIYSYYGYTS | YWGYPYAM |
| 7063 | ITGAM/B2(CD11b) | SVSSA | SASSLYS | WYFLI | LSYSYM | SIYSYYSSTS | SYHSYYAGL |
| 7064 | ITGAM/B2(CD11b) | SVSSA | SASSLYS | WVHGLI | LSYSSM | YIYSSSGYTY | WGWYAHAGM |
| 7065 | ITGAM/B2(CD11b) | SVSSA | SASSLYS | FSSGSWAPI | ISYYYM | SISSSSGYTY | GAM |
| 7055 | ITGAX/B2 | SVSSA | SASSLYS | GPVHHLI | ISYYSI | SISSSYGYTY | SYAM |
| 7056 | ITGAX/B2 | SVSSA | SASSLYS | WGAWGPLI | LYYYSM | YIYPYYGYTS | TVRGSKKPYFSGWAM |
| 7057 | ITGAX/B2 | SVSSA | SASSLYS | YGYYALF | LSYSYM | SIYSYYGSTY | AAGSWVSGGYYFHVGI |

Isotype

| Integrin | IgG | KD (M) | KD Error | kon(1/Ms) | kon Error | kdis(1/s) | kdis Error |
|---|---|---|---|---|---|---|---|
| rhIntegrin alphaL beta2 | 7056 | 2.40E-08 | 1.66E-09 | 4.96E+04 | 3.12E+03 | 1.19E-03 | 3.43E-05 |
| rhIntegrin alphaL beta2 | 7060 | 2.16E-09 | 1.62E-10 | 2.08E+05 | 9.25E+03 | 4.49E-04 | 2.71E-05 |
| rhIntegrin alphaL beta2 | 7062 | 2.91E-09 | 1.92E-10 | 1.75E+05 | 7.28E+03 | 5.10E-04 | 2.62E-05 |
| rhIntegrin alphaL beta2 | 7063 | 1.02E-08 | 4.53E-10 | 1.03E+05 | 3.81E+03 | 1.05E-03 | 2.62E-05 |
| rhIntegrin alphaL beta2 | 7065 | 1.56E-09 | 1.44E-10 | 1.36E+05 | 4.20E+03 | 2.13E-04 | 1.85E-05 |
| rhIntegrin alphaL beta2 | 7341 | 4.07E-09 | 3.84E-10 | 1.81E+05 | 1.25E+04 | 7.36E-04 | 4.73E-05 |
| rhIntegrin alphaM beta2 | 7056 | 6.34E-07 | 1.01E-06 | 7.54E+02 | 1.20E+03 | 4.78E-04 | 1.51E-05 |
| rhIntegrin alphaM beta2 | 7060 | 2.01E-09 | 1.61E-10 | 1.36E+05 | 4.37E+03 | 2.73E-04 | 2.00E-05 |
| rhIntegrin alphaM beta2 | 7062 | 3.20E-09 | 1.87E-10 | 1.03E+05 | 2.80E+03 | 3.29E-04 | 1.70E-05 |
| rhIntegrin alphaM beta2 | 7063 | 1.14E-08 | 4.73E-10 | 5.94E+04 | 1.90E+03 | 6.80E-04 | 1.79E-05 |
| rhIntegrin alphaM beta2 | 7065 | 2.15E-09 | 1.42E-10 | 9.77E+04 | 2.13E+03 | 2.10E-04 | 1.30E-05 |
| rhIntegrin alphaM beta2 | 7341 | 2.75E-09 | 1.98E-10 | 8.36E+04 | 2.20E+03 | 2.30E-04 | 1.54E-05 |
| rhIntegrin alphaX beta2 | 7056 | 5.02E-09 | 2.71E-10 | 5.33E+04 | 1.35E+03 | 2.68E-04 | 1.27E-05 |
| rhIntegrin alphaX beta2 | 7060 | 1.51E-09 | 2.37E-10 | 8.08E+04 | 2.58E+03 | 1.22E-04 | 1.87E-05 |
| rhIntegrin alphaX beta2 | 7062 | 1.46E-09 | 2.29E-10 | 6.91E+04 | 1.96E+03 | 1.01E-04 | 1.56E-05 |
| rhIntegrin alphaX beta2 | 7063 | 3.96E-09 | 3.22E-10 | 4.14E+04 | 1.24E+03 | 1.64E-04 | 1.24E-05 |
| rhIntegrin alphaX beta2 | 7065 | 2.03E-09 | 1.86E-10 | 5.61E+04 | 1.15E+03 | 1.14E-04 | 1.02E-05 |
| rhIntegrin alphaX beta2 | 7341 | 2.80E-09 | 2.80E-10 | 6.72E+04 | 2.16E+03 | 1.88E-04 | 1.78E-05 |

FIG. 6

ANTIBODIES TARGETING INTEGRIN BETA-2

REFERENCE TO SEQUENCE LISTING SUBMITTED ELECTRONICALLY

The content of the electronically submitted Sequence Listing (name: "P1295US_Sequence listing.xml"; size: 38,753 bytes; and date of creation: Nov. 28, 2025), is herein incorporated by reference in its entirety.

TECHNICAL FIELD

The embodiments disclosed herein relate to antibody therapeutics, and, in particular to antibodies that specifically target integrin beta-2.

INTRODUCTION

Development of safe and effective immunotherapies has proven difficult given the lack of characterized cancer-specific surface markers. It has been hypothesized that given aberrancies in tumor signaling, metabolism, or cell-microenvironment communication—all of which heavily involve membrane proteins—cancer-specific surface protein conformations may in fact be widespread. In particular, integrin beta-2, may be a promising immunotherapeutic target, expressed widely across cell lines and patient tumors.

Accordingly, there is a need for novel antibodies that specifically target integrin beta-2 for further development of targeted cancer immunotherapies and diagnostics.

SUMMARY

Phage display selection was used to identify anti-integrin beta-2 antibodies that can be used for diagnostic and therapeutic purposes.

In some embodiments, provided is an anti-integrin beta-2 antibody having a KD less than about 10 nM.

In some embodiments, the antibody includes an anti-integrin beta-2 binding domain having at least one, at least two, or three CDRs of a variable domain sequence of SEQ ID NO:2 or SEQ ID NO:3. In some embodiments, the anti-integrin beta-2 binding domain comprises an HCDR3 of SEQ ID NO:2 and an LCDR3 of SEQ ID NO:3. In some embodiments, the anti-integrin beta-2 binding domain comprises an HCDR1, HCDR2, and HCDR3 of SEQ ID NO:2 and LCDR1, LCDR2, and LCDR3 of SEQ ID NO:3.

In some embodiments, the anti-integrin beta-2 binding domain comprises an HCDR1, HCDR2, and HCDR3 of SEQ ID NO:2 in which one of the CDRs comprises a substitution relative to the corresponding CDR set forth in SEQ ID NO:2. In some embodiments, the anti-integrin beta-2 binding domain comprises an HCDR1, HCDR2, and HCDR3 of SEQ ID NO:2 in which two of the CDRs comprise a substitution relative to the corresponding CDRs set forth in SEQ ID NO:2. In some embodiments, the anti-integrin beta-2 binding domain comprises an HCDR1, HCDR2, and HCDR3 of SEQ ID NO:2 in which all three of the CDRs comprise a substitution relative to the corresponding CDR sequences set forth in SEQ ID NO:2.

In some embodiments, the anti-integrin beta-2 binding domain comprises an LCDR1, LCDR2, and LCDR3 of SEQ ID NO:3 in which one of the CDRs comprises a substitution relative to the corresponding CDR set forth in SEQ ID NO:3. In some embodiments, the anti-integrin beta-2 binding domain comprises an LCDR1, LCDR2, and LCDR3 of SEQ ID NO: 3 in which two of the CDRs comprise a substitution relative to the corresponding CDRs set forth in SEQ ID NO:3. In some embodiments, the anti-integrin beta-2 binding domain comprises an LCDR1, LCDR2, and LCDR3 of SEQ ID NO:3 in which all three of the CDRs comprise a substitution relative to the corresponding CDR sequences set forth in SEQ ID NO:3.

In some embodiments, the anti-integrin beta-2 binding domain comprises a variable region having at least 70%, 75%, 85%, 90%, 91%, 92%, 93%, 94%, 95%, 96%, 97%, 98%, 99%, or 100% sequence identity to the amino acid sequence of a variable region sequence of SEQ ID NO:2 or SEQ ID NO:3. In some embodiments, the variable domain comprises substitutions, insertions, or deletions in the framework of a variable region as shown in SEQ ID NO:2 or SEQ ID NO:3. In some embodiments, the anti-integrin beta-2 binding domain of the present disclosure comprises a heavy chain variable region comprising the HCD1, HCDR2, and HCDR3 sequence of SEQ ID NO:2 and having at least 95% identity to SEQ ID NO:2; and a light chain variable region comprising the LCD1, LCDR2, LCDR3 sequences of SEQ ID NO:3 and having at least 95% identity to SEQ ID NO:3.

Other aspects and features will become apparent, to those ordinarily skilled in the art, upon review of the following description of some exemplary embodiments.

BRIEF DESCRIPTION OF THE DRAWINGS

The drawings included herewith are for illustrating various examples of articles, methods, and apparatuses of the present specification. In the drawings:

FIGS. 2A-2D are representative ELISA plots for phage selected anti-integrin beta-2 antibody candidates;

FIG. 3 is a table showing the complementarity-determining regions (CDRs) of the anti-integrin beta-2 antibody candidates shown in FIGS. 2A-2D.

FIG. 6 is a table showing binding affinities of antibodies against integrin-2 heterodimers from the biolayer interferometry plots shown in FIGS. 5A-5R.

DETAILED DESCRIPTION

Figure 1:
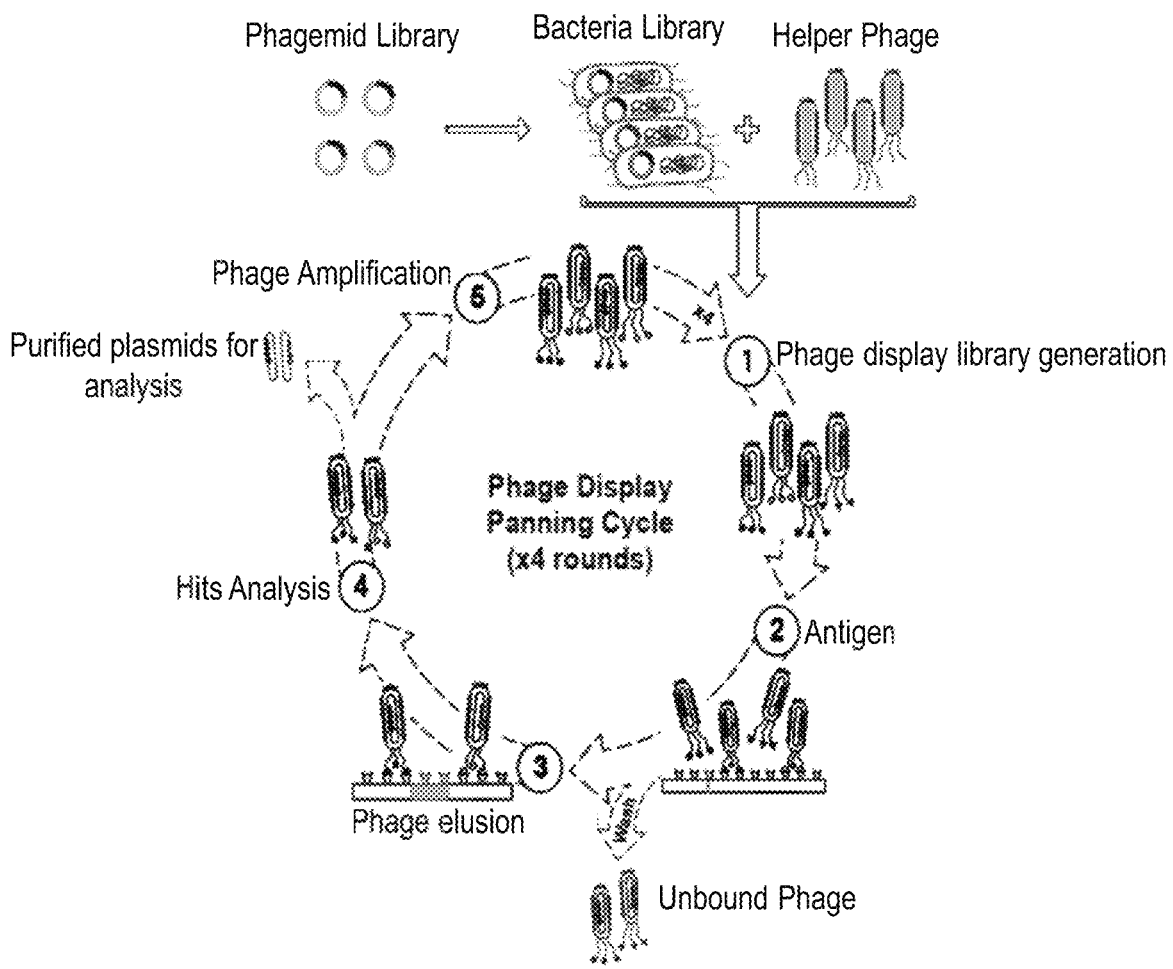
FIG. 1 is a diagram of phage-fab display selection strategy for developing anti-integrin beta-2 antibodies.
Figure 4A:
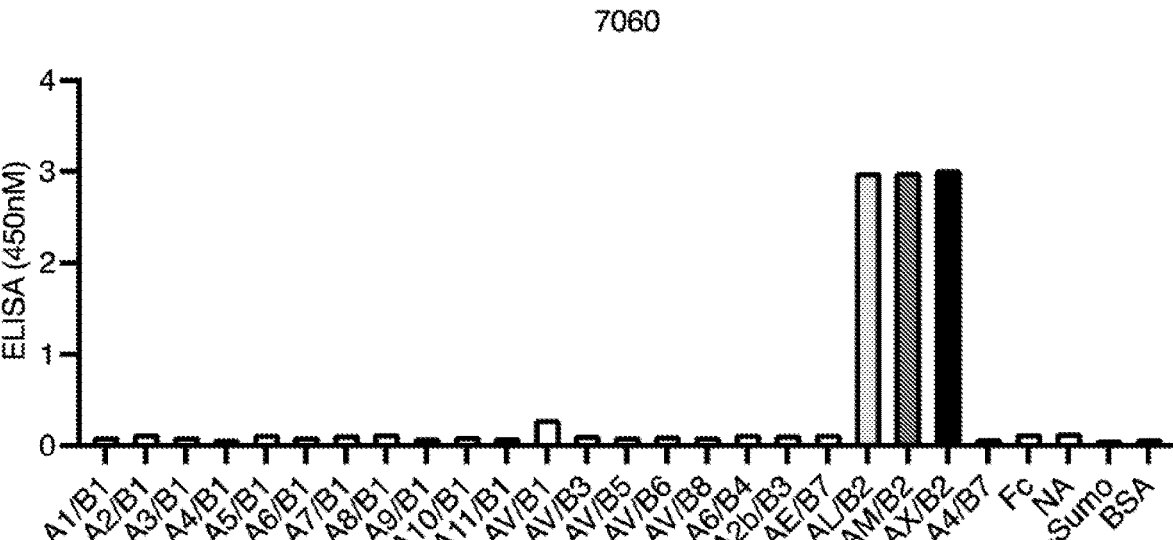
FIGS. 4A-4H are ELISA plots showing integrin beta-2 binding specificity of the antibodies obtained from phage display selection.
Figure 4B:
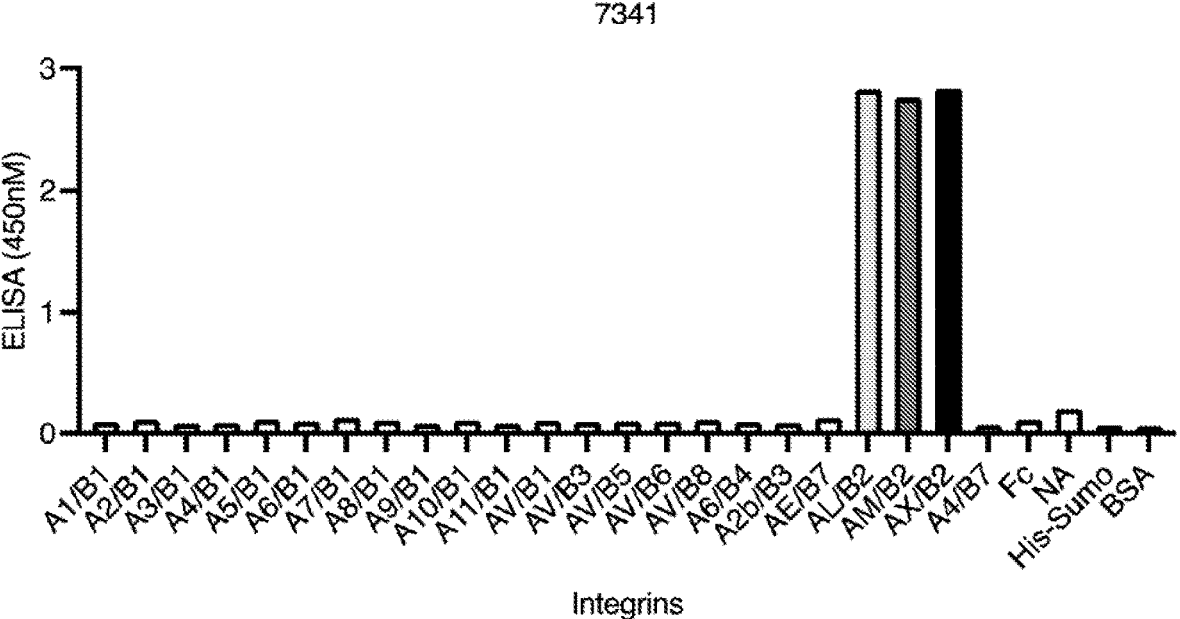
Figure 4C:
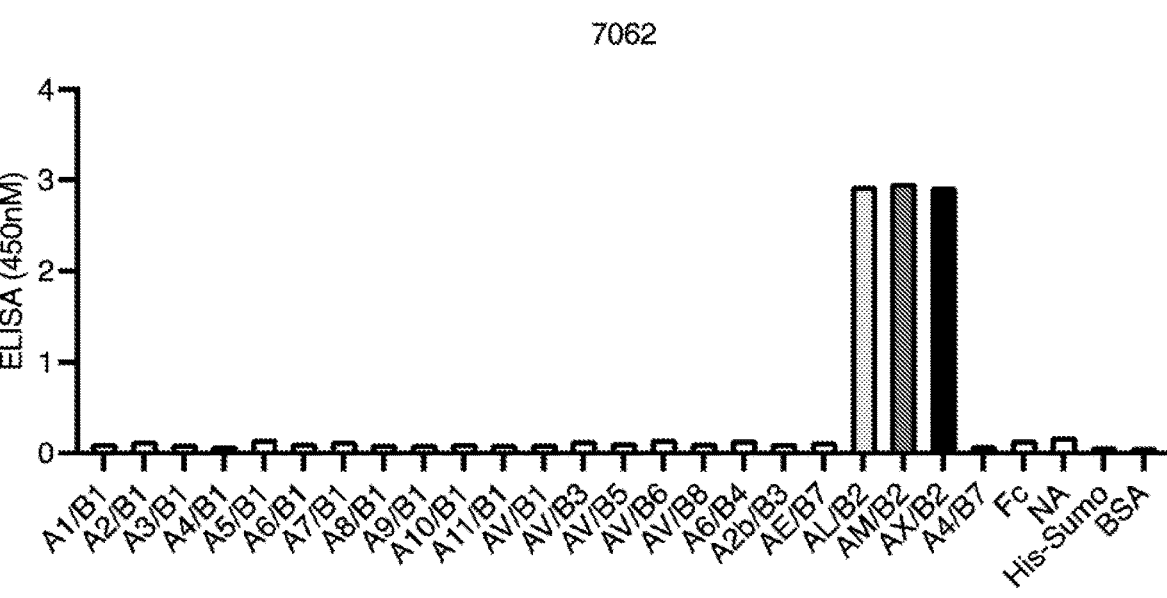
Figure 4D:
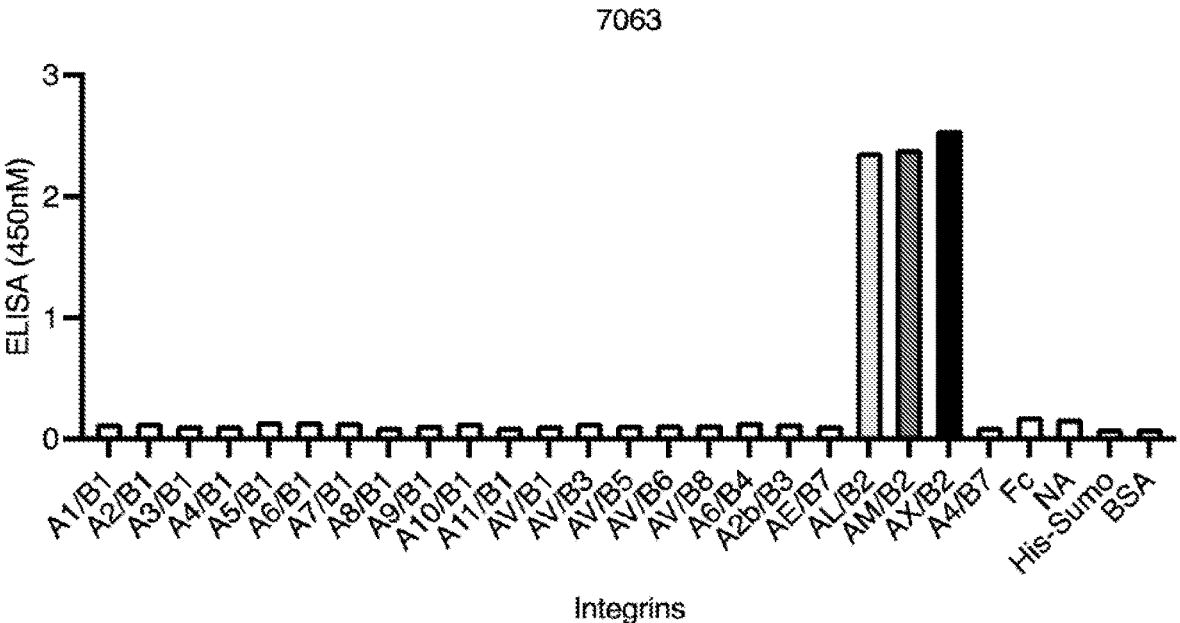
Figure 4E:
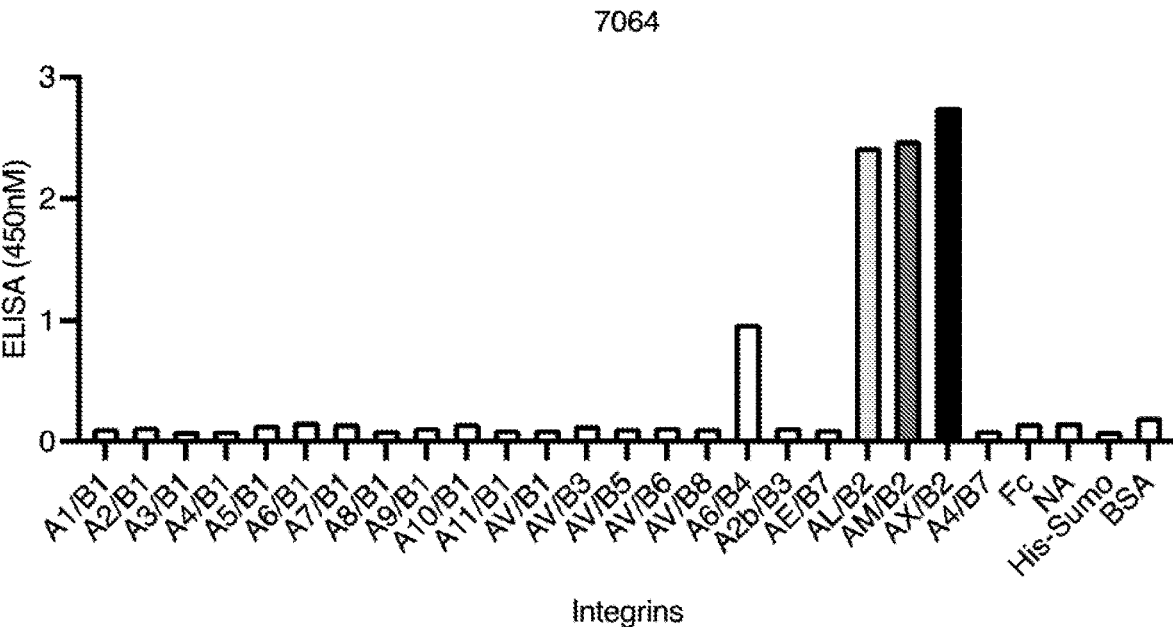
Figure 4F:
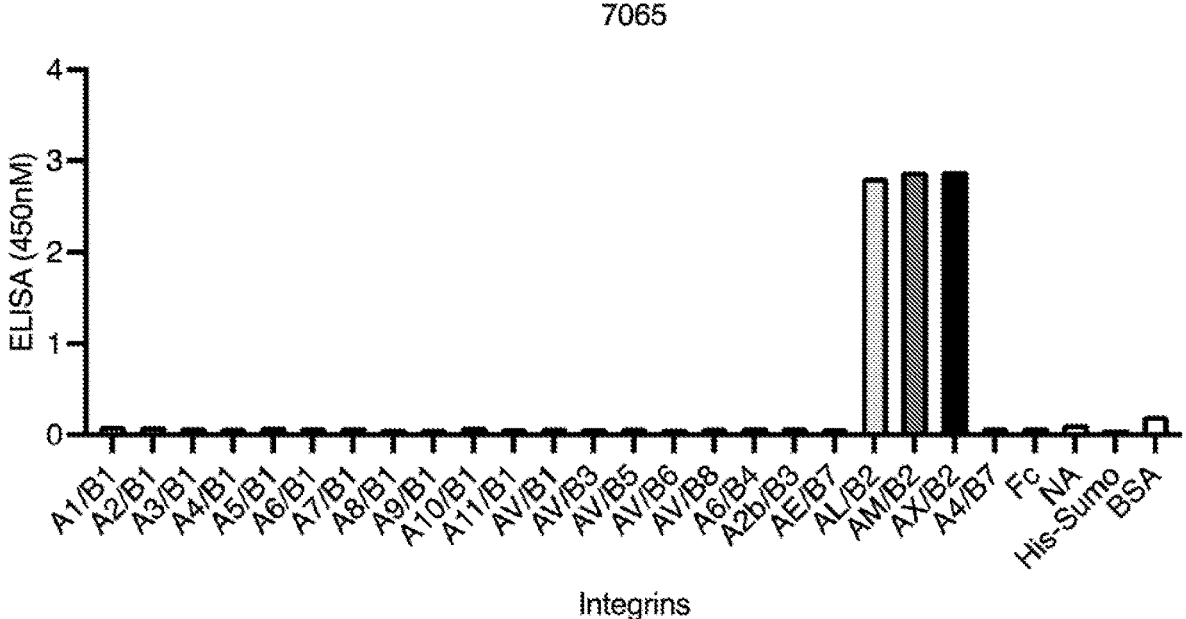
Figure 4G:
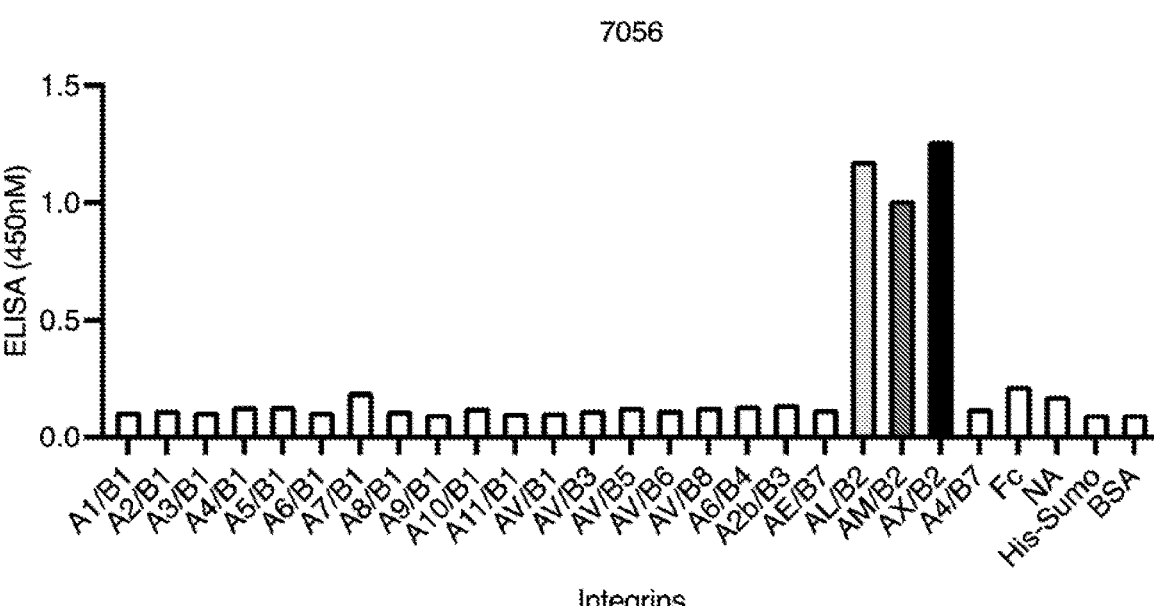
Figure 4H:
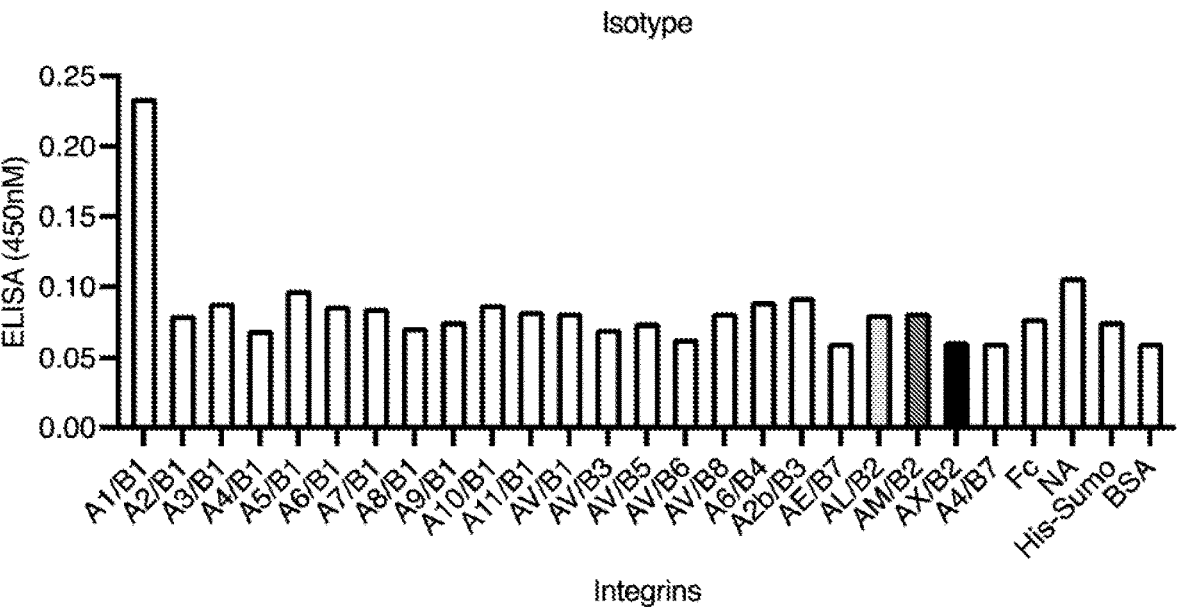

Various compositions of matter will be described below to provide an example of each claimed embodiment. No embodiment described below limits any claimed embodiment and any claimed embodiment may cover compositions that differ from those described below. The claimed embodiments are not limited to compositions having all of the features of any one composition described below or to features common to multiple or all of the compositions described below.

The term "about" as used herein refers to the usual error range for the respective value readily known to the skilled person in this technical field. For example, for KD and IC50 values ±20%, ±10%, or ±5%, are within the intended meaning of the recited value.

The term integrin beta-2 or Integrin beta-2, also known as CD18, LAD, LCAMB, LFA-1, MAC-1, MF17, MFI7, or integrin subunit beta 2, as used herein, refers to a polypeptide that is encoded by a ITGB2 gene (chr21:44,885,949-
44,931,989 (GRCH38/hg38), cytogenetically localized to
human chromosome 21q22.3 by HGNC, Entrez Gene, and
Ensembl (genomic coordinates (GRCh38/hg38 assembly
December 2013:) and plays a role in cell adhesion, cell-
surface-mediated sequencing, and immune responses. An
illustrative human integrin beta-2 protein sequence encoded
by a human ITGB2 gene, P05107-1, is available under
Uniprot number P05107 and is provided as SEQ ID NO: I.
integrin beta-2 can bind to a number of alpha chains and thus
can from multiple heterodimers, but also exists in soluble,
ligand binding forms. Deficiencies in Itgb2 expression can
lead to adhesion defects in circulating white blood cells in
humans, reducing the immune system's ability to fight off
foreign invaders. Illustrative Integrin beta-2 heterodimers
include, e.g., integrin ITGAL/ITGB2, which is a receptor for
ICAM1, ICAM2, ICAM3 and ICAM4, and is also a receptor
for the secreted form of ubiquitin-like protein ISG15; inte-
grins ITGAM/ITGB2 and ITGAX/ITGB2, which are recep-
tors for the iC3b fragment of the third complement compo-
nent and for fibrinogen; integrin ITGAX/ITGB2, which
recognizes the sequence G-P-R in fibrinogen alpha-chain,
Integrin ITGAM/ITGB2, which recognizes P1 and P2 pep-
tides of fibrinogen gamma chain and is also a receptor for
factor X; and integrin ITGAD/ITGB2, which is a receptor
for ICAM3 and VCAM1.

The terms "anti-integrin beta-2 antibody," "integrin
beta-2 specific antibody," "integrin beta-2 antibody," and
"anti-integrin beta-2" are used synonymously herein to refer
to an antibody that specifically binds to integrin beta-2. An
illustrative human integrin beta-2 sequence is provided in
SEQ ID NO:1.

An "anti-integrin beta-2 binding domain" as used herein
refers to an antigen binding domain comprising a $V_H$ and a
$V_L$ region of an anti-integrin beta-2 antibody as described
herein, which antigen binding domain binds to integrin
beta-2.

An anti-integrin beta-2 antibody of the present disclosure
binds to integrin beta-2. An active state of integrin beta-2 is
an extended-open conformation (see, e.g., Nishida et al,
Immunity 25:583-94, 2006; Li et al, EMBO J. 36:629-45,
2017). The active conformation (extended-open) has a
4,000-fold increase in ligand affinity compared to the other
two states (bent-closed, inactive; and extended-closed (inter-
mediate) (Li et al, 2017, supra). Integrin activation takes
place upon cell stimulation through various cell surface
receptors. Cell stimulation triggers an inside-out signaling
pathway that ultimately recruits cytoplasmic factors such as
talin and kindlin to the NPxY motifs of the cytoplasmic tail
of the integrin's beta-chain, which causes the cytoplasmic
tails of the integrin subunits to separate and switches the
integrin to the active (extended-open) conformation.

As used herein, the term "antibody" refers to a polypep-
tide comprising a framework region encoded by an immu-
noglobulin gene, or fragments thereof, that specifically binds
and recognizes an antigen, e.g., integrin beta-2. Typically,
the "variable region" contains the antigen-binding region of
the antibody (or its functional equivalent) and is important
in specificity and affinity of binding. The term "antibody" as
used herein thus encompasses antigen binding fragments,
e.g., an antigen binding domain, or other antigen binding
fragment. Antigen binding fragments may be produced by
modification of whole antibodies, or produced using recom-
binant DNA methodologies (e.g., single chain Fv formats).

An illustrative immunoglobulin (antibody) structural unit
comprises a tetramer. Each tetramer is composed of two
identical pairs of polypeptide chains, each pair having one

4

"light" (about 25 kD) and one "heavy" chain (about 50-70
kD). The N-terminus of each chain defines a variable region
of about 100 to 110 or more amino acids primarily respon-
sible for antigen recognition. The terms variable light chain
$(V_L)$ and variable heavy chain $(V_H)$ refer to these light and
heavy chains respectively.

As used herein, "V-region" refers to an antibody, e.g.,
antibody, variable region domain comprising the segments
of Framework 1, CDR1, Framework 2, CDR2, and Frame-
work 3, including CDR3 and Framework 4, which segments
are added to the V-segment as a consequence of rearrange-
ment of V-region genes during B-cell differentiation.

As used herein, "complementarity-determining region
(CDR)" refers to the three hypervariable regions that inter-
rupt the four "framework" regions of a variable domain. The
CDRs are the primary contributors to binding to an epitope
of an antigen. The CDRs are referred to as CDR1, CDR2,
and CDR3, numbered sequentially starting from the N-ter-
minus.

The amino acid sequences of the CDRs and framework
regions can be determined using various well-known defi-
nitions in the art, e.g., Kabat, Chothia, international ImMu-
noGeneTics database (IMGT), and AbM (see, e.g., Johnson
et al., supra; Chothia & Lesk, 1987, Canonical structures for
the hypervariable regions of immunoglobulins. J. Mol. Biol.
196, 901-917; Chothia C. et al., 1989, Conformations of
immunoglobulin hypervariable regions. Nature 342, 877-
883; Chothia C. et al., 1992, structural repertoire of the
human VH segments J. Mol. Biol. 227, 799-817; Al-Lazi-
kani et al., J. Mol. Biol 1997, 273(4)). Definitions of antigen
combining sites are also described in the following: Ruiz et
al., IMGT, the international ImMunoGeneTics database.
Nucleic Acids Res., 28, 219-221 (2000); and Lefranc, M.-P.
IMGT, the international ImMunoGeneTics database.
Nucleic Acids Res. January 1; 29(1):207-9 (2001); MacCa-
llum et al, Antibody-antigen interactions: Contact analysis
and binding site topography, J. Mol. Biol., 262 (5), 732-745
(1996); and Martin et al, Proc. Natl Acad. Sci. USA, 86,
9268-9272 (1989); Martin, et al, Methods Enzymol., 203,
121-153, (1991); Pedersen et al, Immunomethods, 1, 126,
(1992); and Rees et al, In Sternberg M. J. E. (ed.), Protein
Structure Prediction. Oxford University Press, Oxford, 141-
172 1996). Reference to CDRs as determined by Kabat
numbering are based, for example, on Kabat et al.,
Sequences of Proteins of Immunological Interest, 5th Ed.
Public Health Service, National Institute of Health,
Bethesda, MD (1991)). Chothia CDRs are determined as
defined by Chothia (see, e.g., Chothia and Lesk J. Mol. Biol.
196:901-917 (1987)).

An "isotype," as used herein, is a class of antibodies
defined by the heavy chain constant region. Antibodies
described herein can be of any isotype of isotype class.
Immunoglobulin genes include the kappa, lambda, alpha,
gamma, delta, epsilon, and mu constant region genes. Light
chains are classified as either kappa or lambda. Heavy chains
are classified as gamma, mu, alpha, delta, or epsilon, which
in turn define the isotype classes, IgG, IgM, IgA, IgD and
IgE, respectively. In some embodiments, the IgG is an IgGl,
IgG2, IgG3 or IgG4.

Antibodies can exist as intact immunoglobulins or as any
of a number of well-characterized fragments that include
specific antigen-binding activity. Such fragments can be
produced by digestion with various peptidases. Pepsin
digests an antibody below the disulfide linkages in the hinge
region to produce F(ab)'2, a dimer of Fab which itself is a
light chain joined to $V_H$-$C_H1$ by a disulfide bond. The
F(ab)'2 may be reduced under mild conditions to break the disulfide linkage in the hinge region, thereby converting the F(ab)'2 dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology.

Antibodies or antigen-binding molecules of the present invention further includes one or more immunoglobulin chains that are chemically conjugated to, or expressed as, fusion proteins with other proteins. It also includes bispecific antibody. A bispecific or bifunctional antibody is an artificial hybrid antibody having two different heavy/light chain pairs and two different binding sites. Other antigen-binding fragments or antibody portions of the invention include single chain variable fragments (scFv) bivalent scFv (diabody), bispecific scFv antibodies where the antibody molecule recognizes two different epitopes, single binding domains (dAbs), and minibodies. The term "antibody" additionally encompasses bispecific and multispecific antibodies as well as any other monovalent, bivalent, or multivalent antibody format.

The various antibodies or antigen-binding fragments described herein can be produced by enzymatic or chemical modification of the intact antibodies, or synthesized de novo using recombinant DNA methodologies (e.g., single chain Fv), or identified using yeast or phage display libraries (see, e.g., McCafferty et al., Nature 348:552-554, 1990; Boder, et al (2000) Proc. Natl. Acad. Sci. U S. A. 97:10701). For example, minibodies can be generated using methods described in the art, e.g., Vaughan and Sollazzo, Comb Chem High Throughput Screen. 4:417-30 2001. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992). Single chain antibodies can be identified using phage display libraries, yeast display, or ribosome display libraries, gene shuffled libraries. Such libraries can be constructed from synthetic, semi-synthetic or native and immunocompetent sources.

A "monoclonal antibody" refers to a clonal preparation of antibodies with a single binding specificity and affinity for a given epitope on an antigen.

A "chimeric antibody" is an antibody molecule in which (a) the constant region, or a portion thereof, is altered, replaced or exchanged so that the antigen binding site (variable region, CDR, or portion thereof) is linked to a constant region of a different or altered class, effector function and/or species, or an entirely different molecule which confers new properties to the chimeric antibody (e.g., an enzyme, toxin, hormone, growth factor, drug, etc.); or (b) the variable region, or a portion thereof, is altered, replaced or exchanged with a variable region having a different or altered antigen specificity (e.g., CDR and framework regions from different species).

A "humanized" antibody is an antibody that retains the reactivity of a non-human antibody while being less immunogenic in humans. This can be achieved, for instance, by retaining the non-human CDR regions and replacing the remaining parts of the antibody with their human counterparts. In one embodiment, some, most or all of the amino acids outside the CDR domains are replaced with amino acids corresponding to the human immunoglobulin germ line, while amino acids within one or more CDR regions are unchanged. In some embodiments, one or more CDR residues may be altered, e.g., to provide a sequence closer to germline or to replace a residue that may impede production.

The term "specifically bind(s)" or "specially target(s)" refers to a molecule (e.g., antibody or antibody fragment) that binds to a target with at least 2-fold greater affinity than non-target compounds, e.g., at least 4-fold, 5-fold, 6-fold, 7-fold, 8-fold, 9-fold, 10-fold, 20-fold, 25-fold, 50-fold, or 100-fold greater affinity. For example, an antibody that specifically binds integrin beta-2, typically bind to integrin beta-2, with at least a 2-fold greater affinity than a non-integrin beta-2 target, or in the case of an antibody that specifically binds active Integrin beta-2, an inactive form of integrin beta-2. In some embodiments, an antibody binds to active Integrin beta-2 with a KD that is at least 100-fold greater than its affinity inactive integrin beta-2.

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

The term "valency" as used herein refers to the number of different binding sites of an antibody for an antigen. A monovalent antibody comprises one binding site for an antigen. A multivalent antibody comprises multiple binding sites.

The words "protein", "peptide", and "polypeptide" are used interchangeably to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

A "flexible linker" as used herein refers to an amino acid sequence that joins domains to provide a certain degree of movement or interaction. Such linkers are generally composed of small, non-polar (e.g., Gly) or polar (e.g., Ser or Thr) amino acids, but may also comprise polar amino acids such as Lys and Glu, e.g., to improve solubility. The small size of these amino acids provides flexibility, and allows for mobility of the connecting functional domains. The incorporation of Ser or Thr can maintain the stability of the linker in aqueous solutions by forming hydrogen bonds with the water molecules, and therefore reduces the unfavorable interaction between the linker and the protein moieties. In some embodiments, flexible linkers are primarily composed of stretches of Gly and Ser residues ("GS" linker). An example of the most widely used flexible linker has the sequence of (Gly-Gly-Gly-Gly-Ser)n. By adjusting the copy number "n", the length of this GS linker can be adjusted to achieve appropriate separation of the functional domains and/or to maintain necessary inter-domain interactions. Besides the GS linkers, many other flexible linkers have been designed for recombinant protein expression.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, y-carboxyglutamate, and 0-phosphoserine. Amino acid analogs refers to compounds that have the same basic chemical structure as a naturally occurring amino acid, e.g., an a carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide is implicit in a described sequence with respect to the expression product, but not with respect to actual probe sequences.

A "substitution" as used herein refers to a substitution of an amino acid such that charge, hydrophobicity, and/or size of the side group chain is maintained. Illustrative sets of amino acids that may be substituted for one another include (i) positively-charged amino acids Lys, Arg and His; (ii) negatively charged amino acids Glu and Asp; (iii) aromatic amino acids Phe, Tyr and Trp; (iv) nitrogen ring amino acids His and Trp; (v) large aliphatic nonpolar amino acids Val, Leu and Ile; (vi) slightly polar amino acids Met and Cys; (vii) small-side chain amino acids Ser, Thr, Asp, Asn, Gly, Ala, Glu, Gln and Pro; (viii) aliphatic amino acids Val, Leu, Ile, Met and Cys; and (ix) small hydroxyl amino acids Ser and Thr. Reference to the charge of an amino acid in this paragraph refers to the charge at physiological pH.

The terms "nucleic acid" and "polynucleotide" are used interchangeably and as used herein refer to both sense and anti-sense strands of RNA, cDNA, genomic DNA, and synthetic forms and mixed polymers of the above. In particular embodiments, a nucleotide refers to a ribonucleotide, deoxynucleotide or a modified form of either type of nucleotide, and combinations thereof. The terms also include, but is not limited to, single- and double-stranded forms of DNA. In addition, a polynucleotide, e.g., a cDNA or mRNA, may include either or both naturally occurring and modified nucleotides linked together by naturally occurring and/or non-naturally occurring nucleotide linkages. Nucleic acid molecules, e.g. oligonucleotide probes or primers, may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analogue, nucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). The above term is also intended to include any topological conformation, including single-stranded, double-stranded, partially duplexed, triplex, hairpinned, circular and padlocked conformations. A reference to a nucleic acid sequence encompasses its complement unless otherwise specified. Thus, a reference to a nucleic acid molecule having a particular sequence should be understood to encompass its complementary strand, with its complementary sequence. The term also includes codon-optimized nucleic acids that encode the same polypeptide sequence.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. A "vector" as used here refers to a recombinant construct in which a nucleic acid sequence of interest is inserted into the vector. Certain vectors are capable of directing the expression of nucleic acids to which they are operatively linked. Such vectors are referred to herein as "expression vectors".

The terms "identical" or "percent identity," in the context of two or more nucleic acids, or two or more polypeptides, refer to two or more sequences or subsequences that are the same or have a specified percentage of nucleotides, or amino acids, that are the same (i.e., about 60% identity, preferably 65%, 70%, 75%, 80%, 85%, 90%, 91% 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters, or by manual alignment and visual inspection. See e.g., the NCBI web site at ncbi.nlm.nih.gov/BLAST. Such sequences are then said to be "substantially identical." This definition also refers to, or may be applied to, the compliment of a nucleotide test sequence. The definition also includes sequences that have deletions and/or additions, as well as those that have substitutions. As described below, the algorithms can account for gaps and the like. Typically, identity exists over a region comprising an antibody epitope, or a sequence that is at least about 25 amino acids or nucleotides in length, or over a region that is 50-100 amino acids or nucleotides in length, or over the entire length of the reference sequence.

The terms "corresponding to," "determined with reference to," or "numbered with reference to" when used in the context of the identification of a given amino acid residue in a polypeptide sequence, refers to the position of the residue of a specified reference sequence when the given amino acid sequence is maximally aligned and compared to the reference sequence. Thus, for example, an amino acid residue in a variable domain polypeptide "corresponds to" an amino acid in the variable domain polypeptide of SEQ ID NO:1 when the residue aligns with the amino acid in SEQ ID NO:1 when optimally aligned to SEQ ID NO:1. The polypeptide that is aligned to the reference sequence need not be the same length as the reference sequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The term "isolated," when applied to a nucleic acid or protein, denotes that the nucleic acid or protein is essentially free of other cellular components with which it is associated in the natural state. It is preferably in a homogeneous state. It can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Subject," "patient," "individual" and like terms are used interchangeably and refer to, except where indicated, mammals such as humans and non-human primates, as well as rabbits, rats, mice, goats, pigs, and other mammalian species. The term does not necessarily indicate that the subject has been diagnosed with a particular disease, but typically refers to an individual under medical supervision. A patient can be an individual that is seeking treatment, monitoring, adjustment or modification of an existing therapeutic regimen, etc.

"Cancer", "tumor," "transformed" and like terms include precancerous, neoplastic, transformed, and cancerous cells, and can refer to a solid tumor, or a non-solid cancer. Cancer includes both benign and malignant neoplasms (abnormal growth). The term "cancer" can thus refer to carcinomas, sarcomas, adenocarcinomas, lymphomas, leukemias, solid and lymphoid cancers, etc. Examples of different types of cancer include, but are not limited to, lung cancer (e.g., non-small cell lung cancer or NSCLC), ovarian cancer, prostate cancer, colorectal cancer, liver cancer (i.e., hepato-carcinoma), renal cancer (i.e., renal cell carcinoma), bladder cancer, breast cancer, thyroid cancer, pleural cancer, pancreatic cancer, uterine cancer, cervical cancer, testicular cancer, anal cancer, pancreatic cancer, bile duct cancer, gastrointestinal carcinoid tumors, esophageal cancer, gall bladder cancer, appendix cancer, small intestine cancer, stomach (gastric) cancer, cancer of the central nervous system, skin cancer, choriocarcinoma; head and neck cancer, blood cancer, osteogenic sarcoma, fibrosarcoma, neuroblastoma, glioma, melanoma, B-cell lymphoma, non-Hodgkin's lymphoma, Burkitt's lymphoma, Small Cell lymphoma, Large Cell lymphoma, monocytic leukemia, myelogenous leukemia, acute lymphocytic leukemia, acute myelocytic leukemia (AML), chronic myeloid leukemia (CML), and multiple myeloma. In some embodiments, the antibody compositions and methods described herein can be used for treating cancer.

The terms "chimeric antigen receptor" and "CAR", used interchangeably herein, refer to artificial multi-module molecules capable of triggering or inhibiting the activation of an immune cell which generally but not exclusively comprise an extracellular domain (e.g., a ligand/antigen binding domain), a transmembrane domain and one or more intracellular signaling domains. The term CAR is not limited specifically to CAR molecules but also includes CAR variants. CAR variants include split CARs wherein the extracellular portion (e.g., the ligand binding portion) and the intracellular portion (e.g., the intracellular signaling portion) of a CAR are present on two separate molecules. CAR variants also include ON-switch CARs which are conditionally activatable CARs, e.g., comprising a split CAR wherein conditional hetero-dimerization of the two portions of the split CAR is pharmacologically controlled. CAR variants also include bispecific CARs, which include a secondary CAR binding domain that can either amplify or inhibit the activity of a primary CAR. CAR variants also include inhibitory chimeric antigen receptors (iCARs) which may, e.g., be used as a component of a bispecific CAR system, where binding of a secondary CAR binding domain results in inhibition of primary CAR activation. CAR molecules and derivatives thereof (i.e., CAR variants) are described, e.g., in PCT Application No. US2014/016527; Fedorov et al. Sci Transl Med (2013); 5(215):215ra172; Glienke et al. Front Pharmacol (2015) 6:21; Kakarla & Gottschalk 52 Cancer J (2014) 20(2):151-5; Riddell et al. Cancer J (2014) 20(2):141-4; Pegram et al. Cancer J (2014) 20(2):127-33; Cheadle et al. Immunol Rev (2014) 257(1):91-106; Barrett et al. Annu Rev Med (2014) 65:333-47; Sadelain et al. Cancer Discov (2013) 3(4):388-98; Cartellieri et al., J Biomed Biotechnol (2010) 956304; the disclosures of which are incorporated herein by reference in their entirety.

As used herein, the term "immune cells" generally includes white blood cells (leukocytes) which are derived from hematopoietic stem cells (HSC) produced in the bone marrow "Immune cells" includes, e.g., lymphocytes (T cells, B cells, natural killer (NK) cells) and myeloid-derived cells (neutrophil, eosinophil, basophil, monocyte, macrophage, dendritic cells).

"T cell" includes all types of immune cells expressing CD3 including T-helper cells (CD4+ cells), cytotoxic T-cells (CD8+ cells), T-regulatory cells (Treg) and gamma-delta T cells.

A "cytotoxic cell" includes CD8+ T cells, natural-killer (NK) cells, and neutrophils, which cells are capable of mediating cytotoxicity responses.

Phage Display Selections of Anti-Integrin Beta-2 Antibodies

Referring to FIG. 1, illustrated therein is a diagram of a phage display selection strategy used for developing anti-integrin beta-2 antibodies. A previously-described Fab-phage display platform (Persson, et al., *J. Mol. Biol.* 425: 803-811, 2013), based on a fully human framework sequence, was used to perform selections versus recombinant integrin beta-2, including Integrin beta-2/Integrin alpha-M (R and D 4047-AM, Antibody #7061, #7062, #7063, #7064 #7065), Integrin-B2/Integrin alpha-L (R and D 3868-AV, Antibody #7060, #7341) and Integrin-B2/Integrin alpha-X (R and D 5755-AX, Antibody #7055, #7056, #7057) recombinant heterodimer protein complexes.

Briefly, integrin beta-2 recombinant protein complexes were immobilized on Maxisorp Immuno plates (ThermoFisher, 12-565-135) and used for positive binding selections with library phage pools that were first exposed to neutravidin coated wells to deplete nonspecific binders. After four rounds of binding selections, clonal phage was prepared and evaluated by phage ELISA and sequencing as previously described (Persson, et al., supra) and summarized below.

Figure 5A:
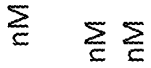
FIG. 5A-5R are representative biolayer interferometry plots showing binding kinetics of antibodies against integrin-2 heterodimers.
Figure 5B:
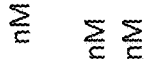
Figure 5C:
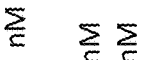
Figure 5D:
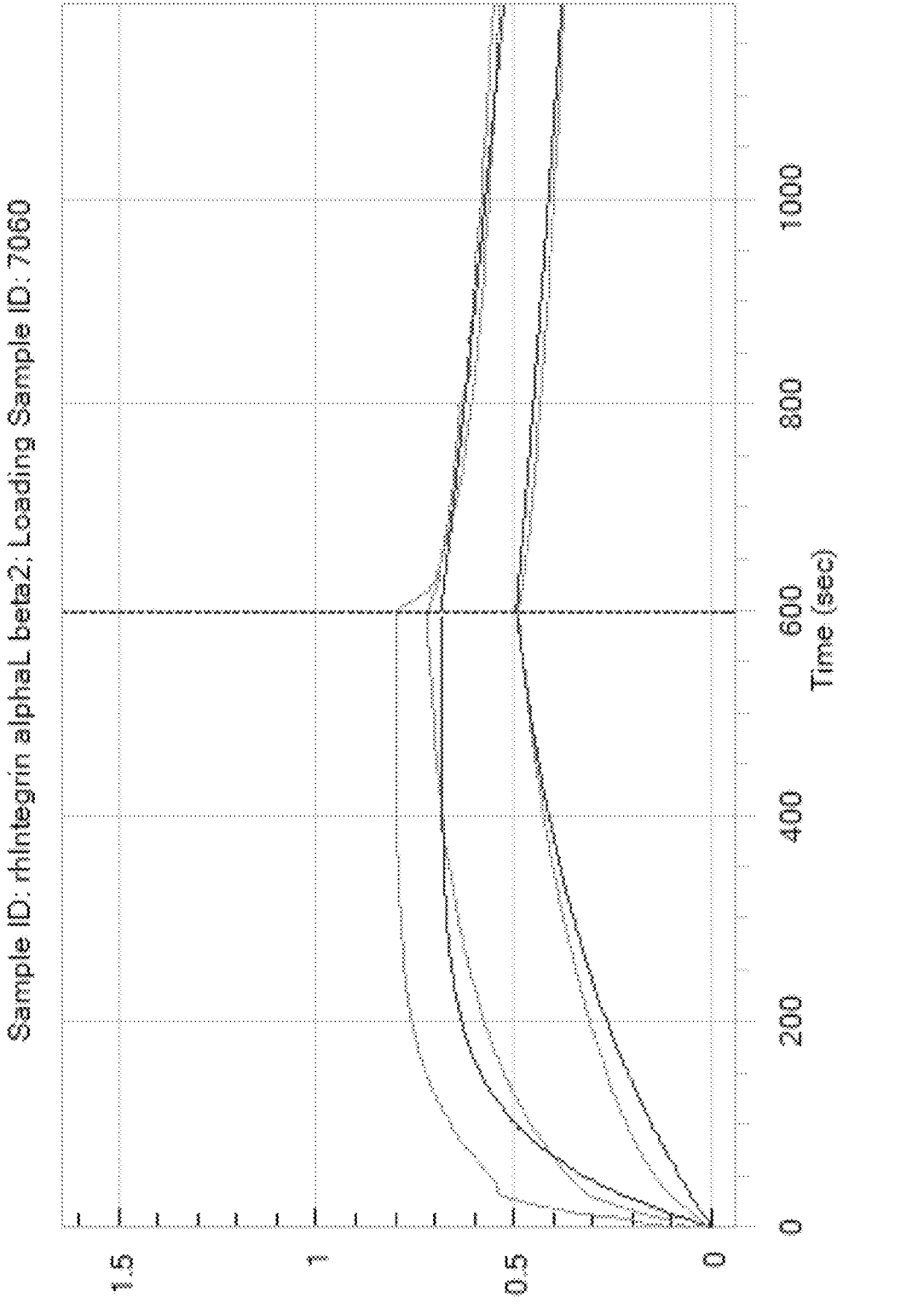
Figure 5E:
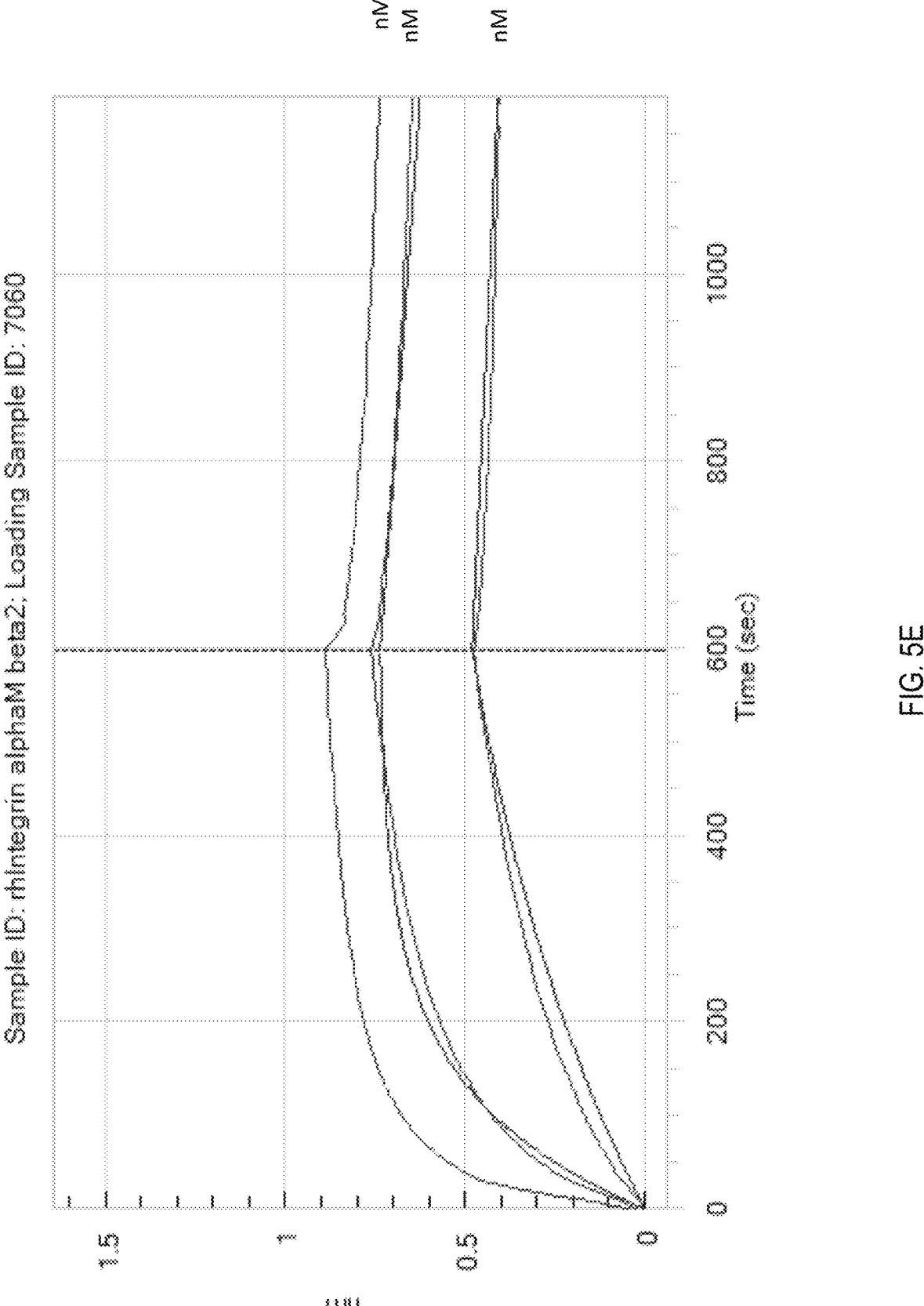
Figure 5F:
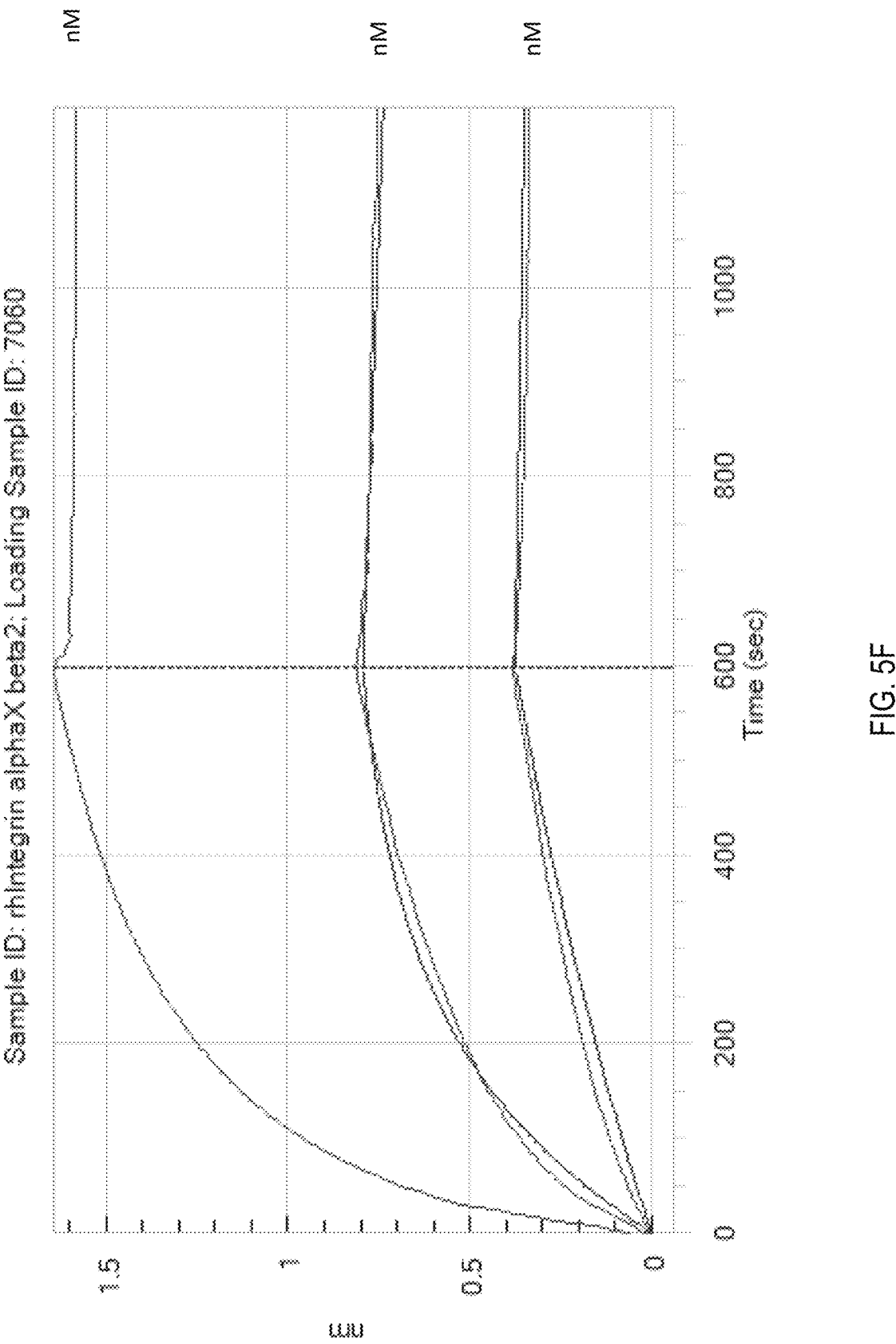
Figure 5G:
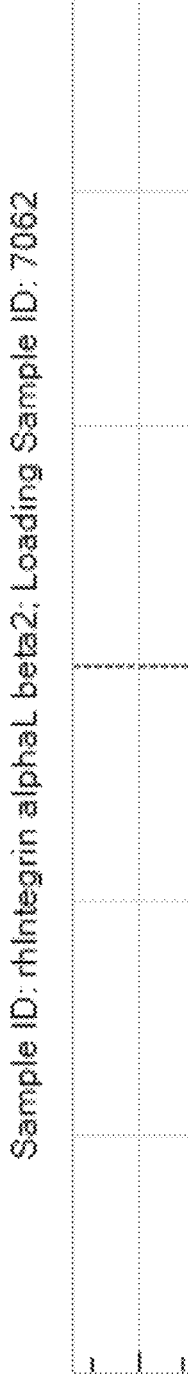
Figure 5H:
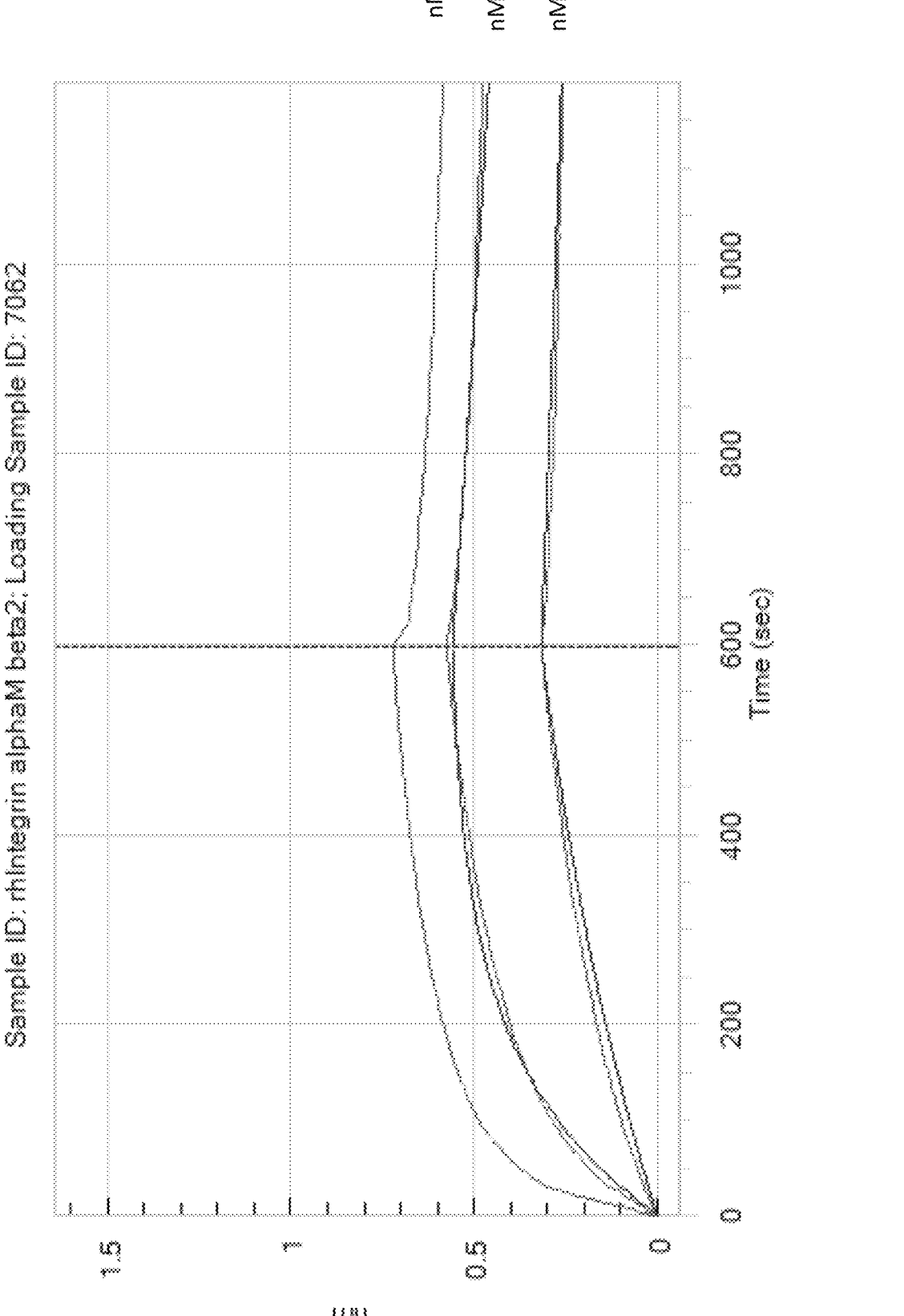
Figure 51:
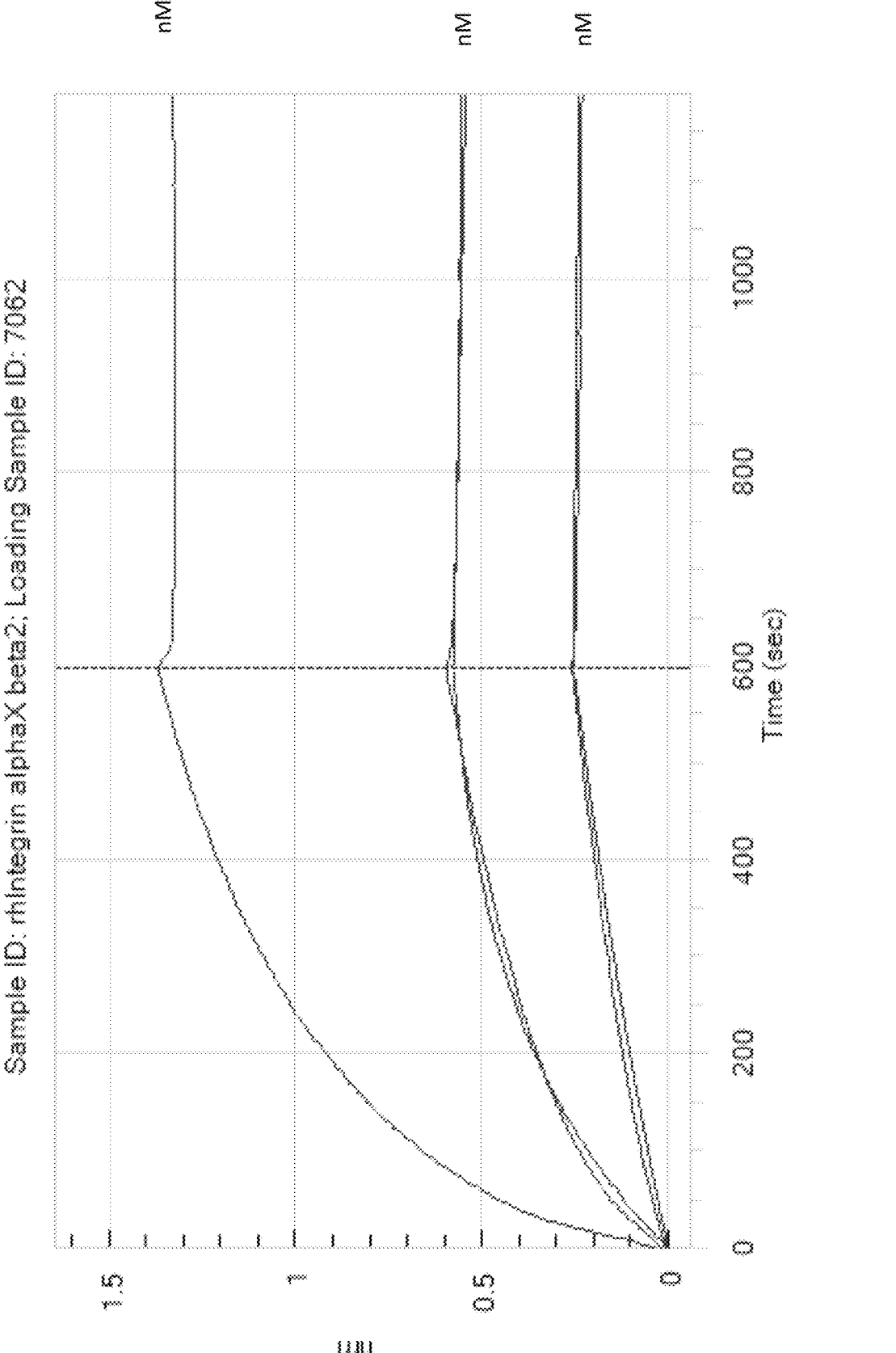
Figure 5J:
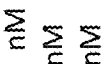
Figure 5K:
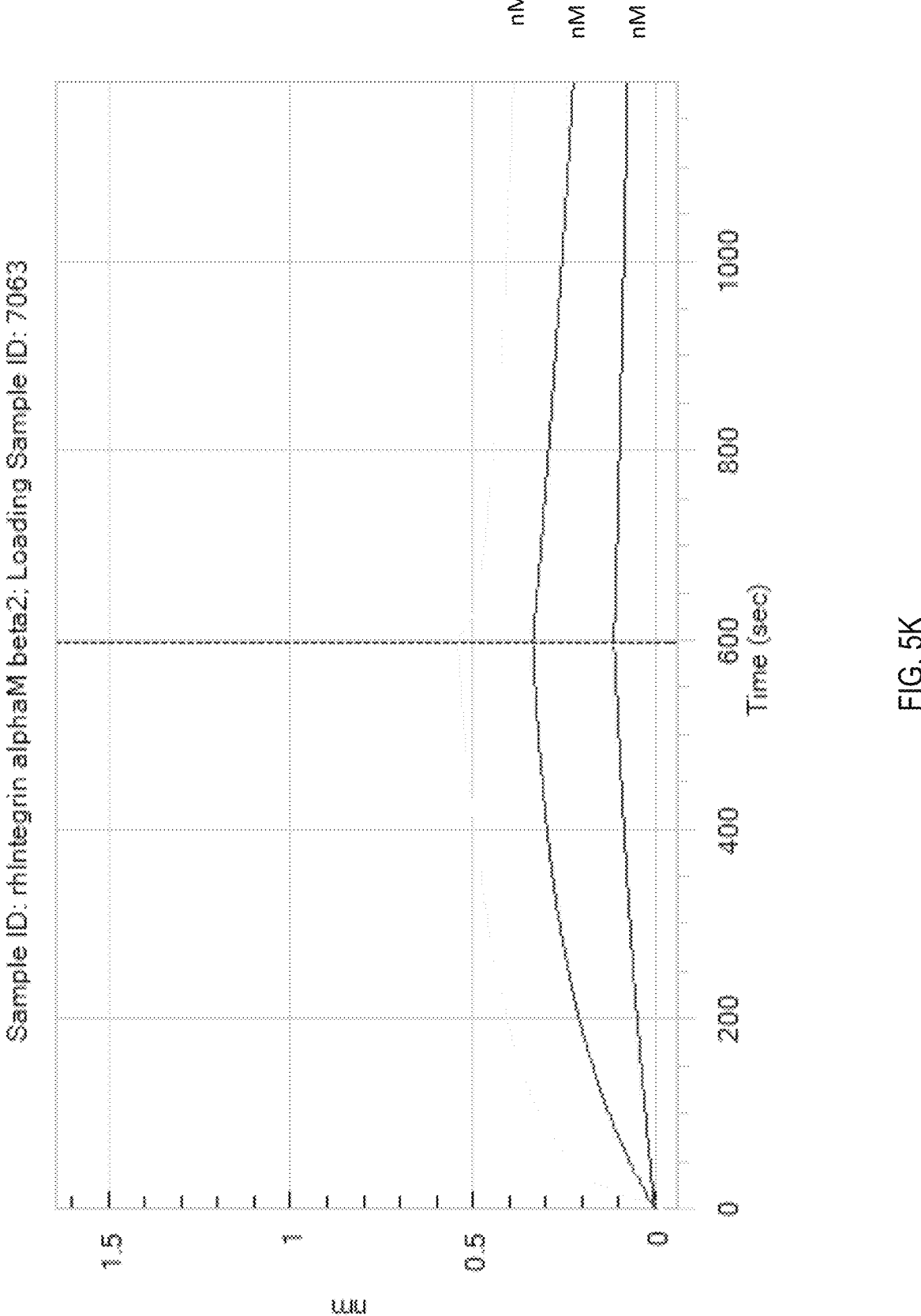
Figure 5L:
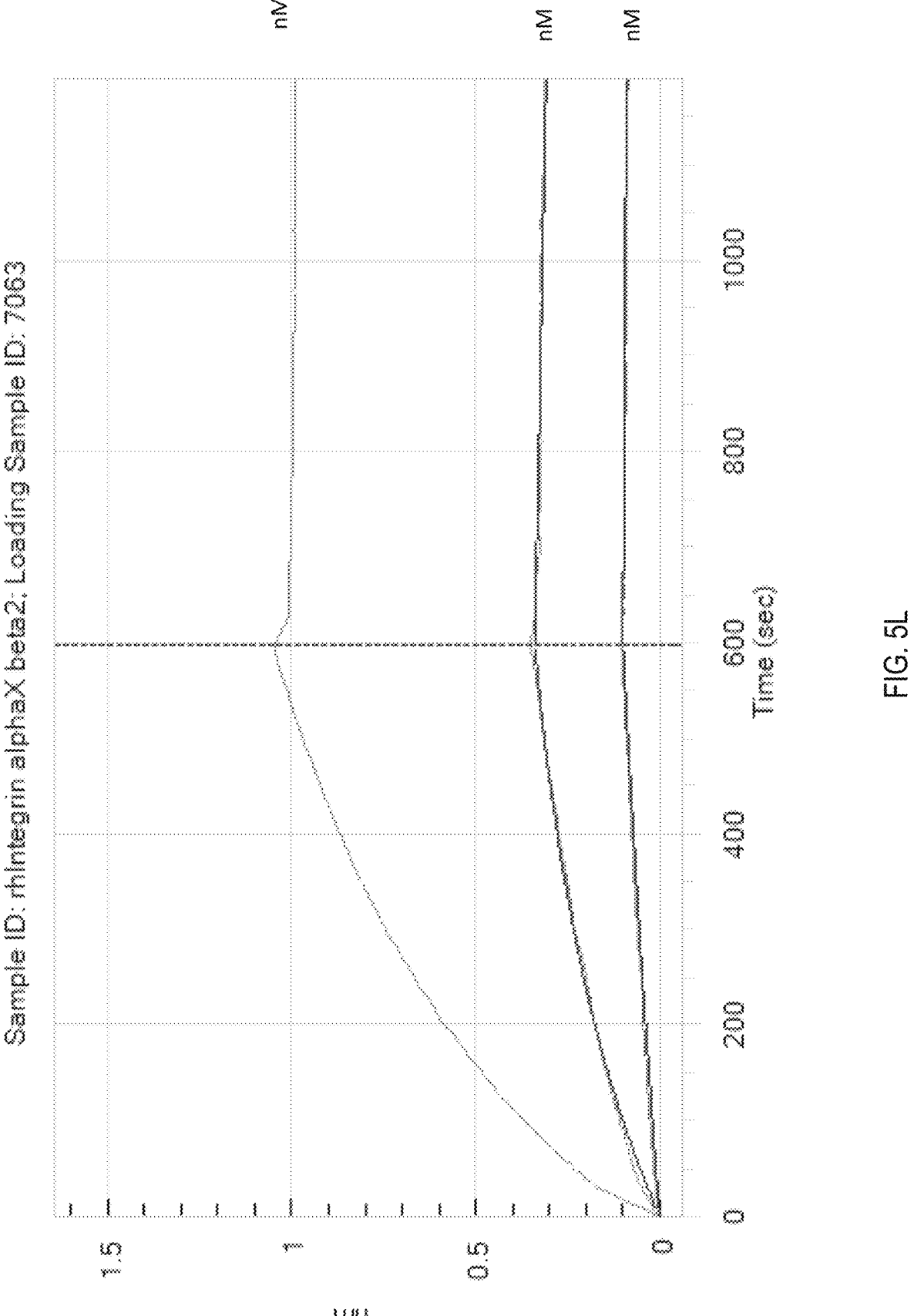
Figure 5M:
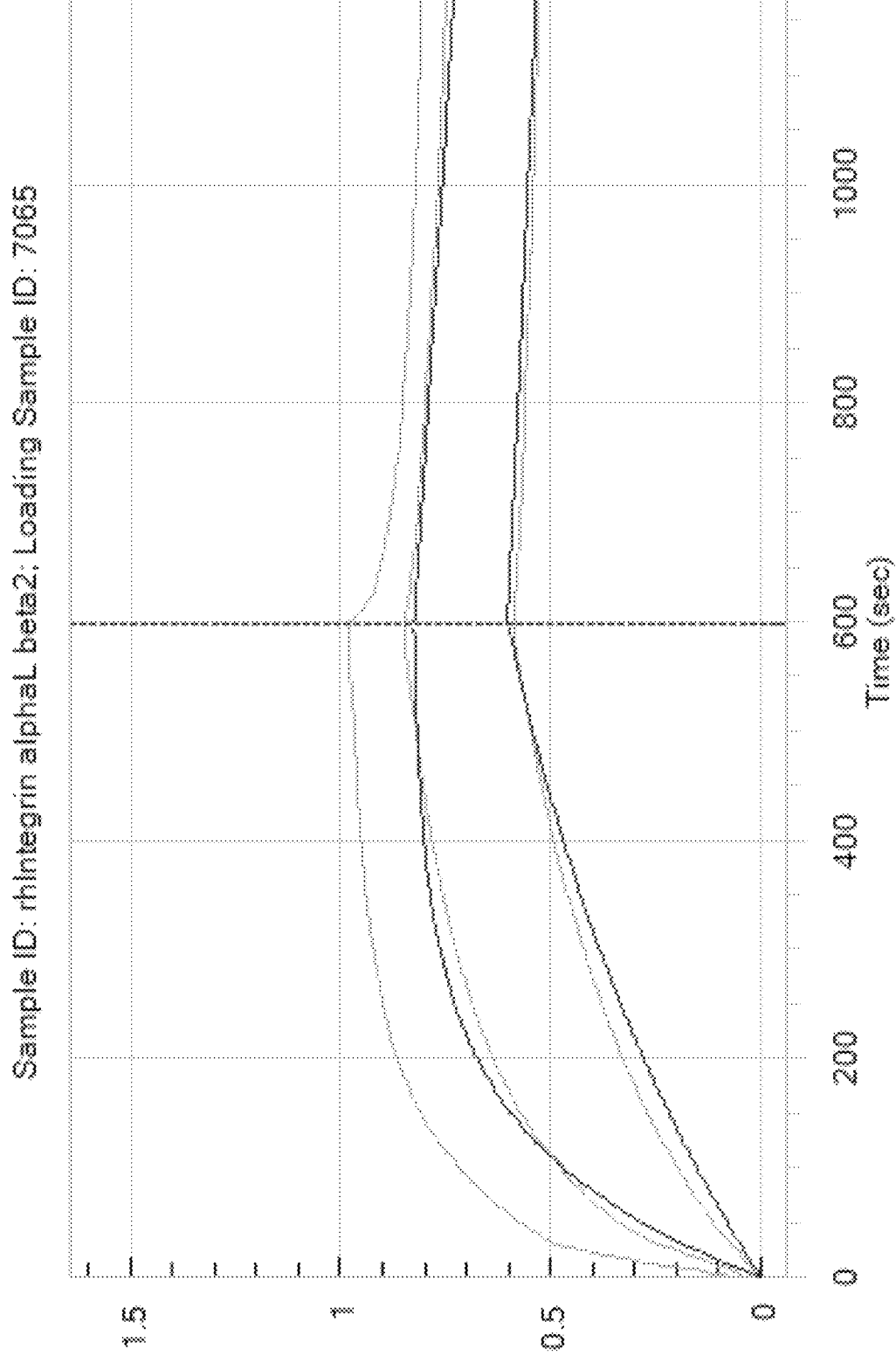
Figure 5N:
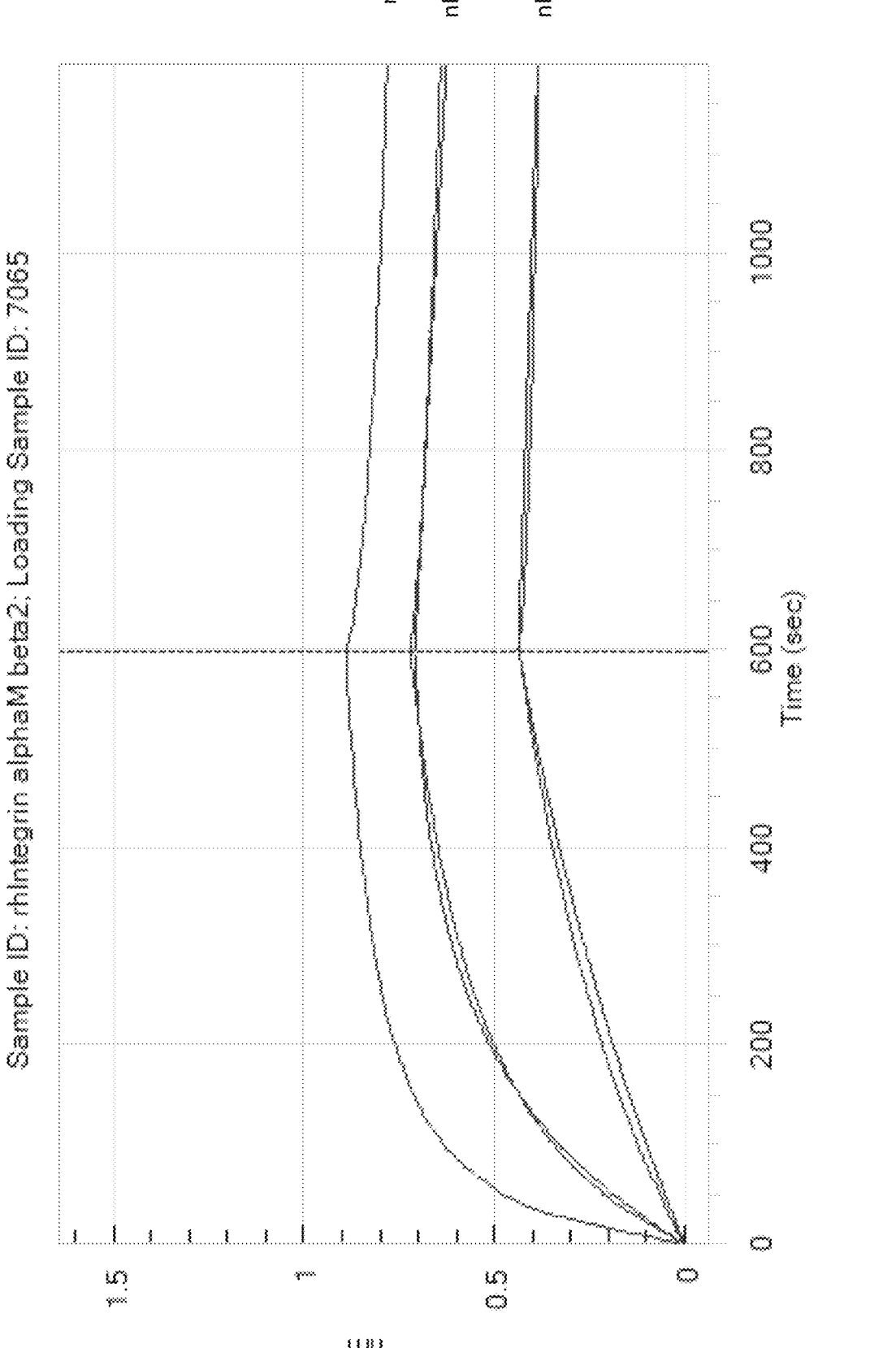
Figure 50:
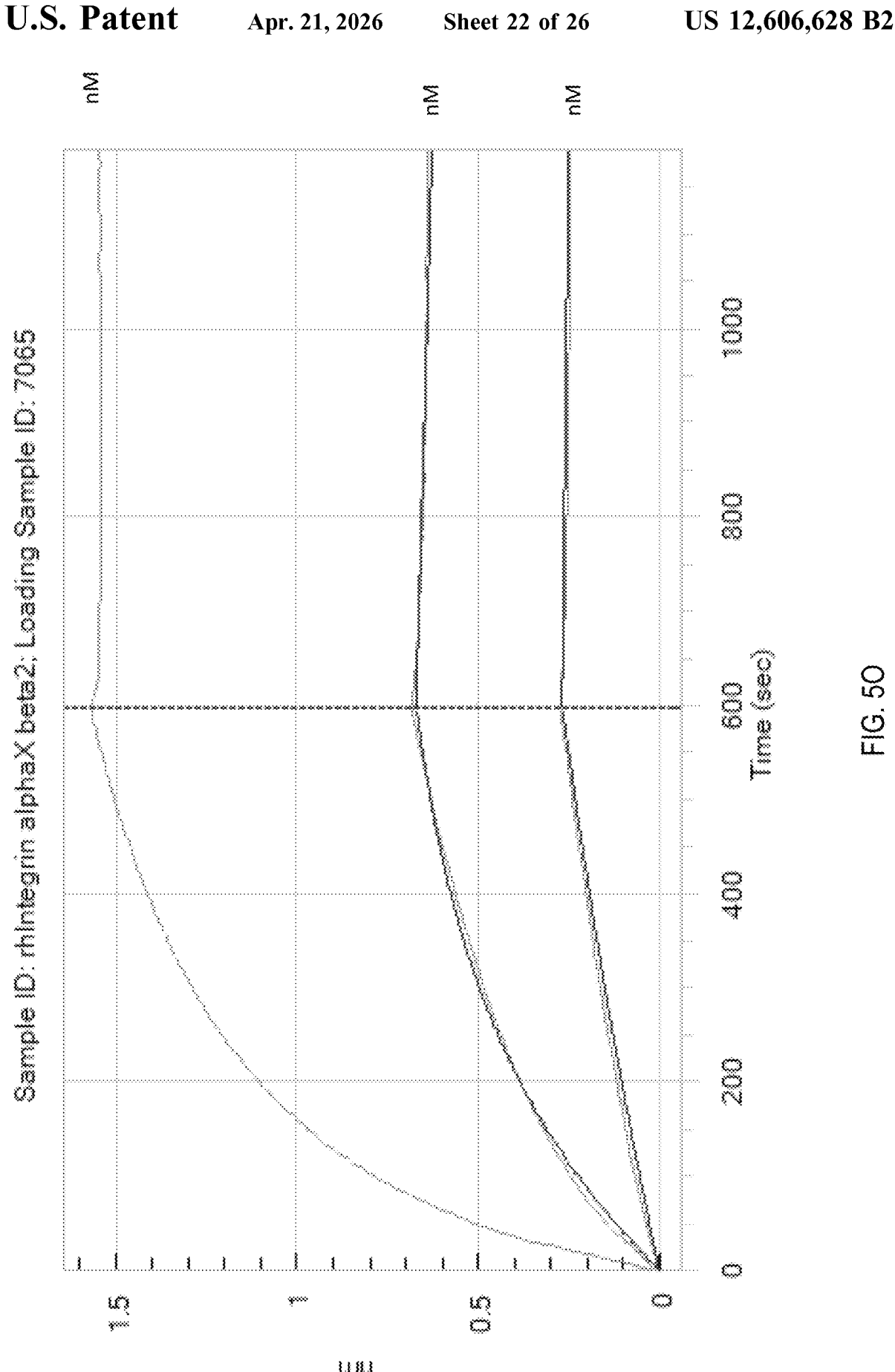
Figure 5P:
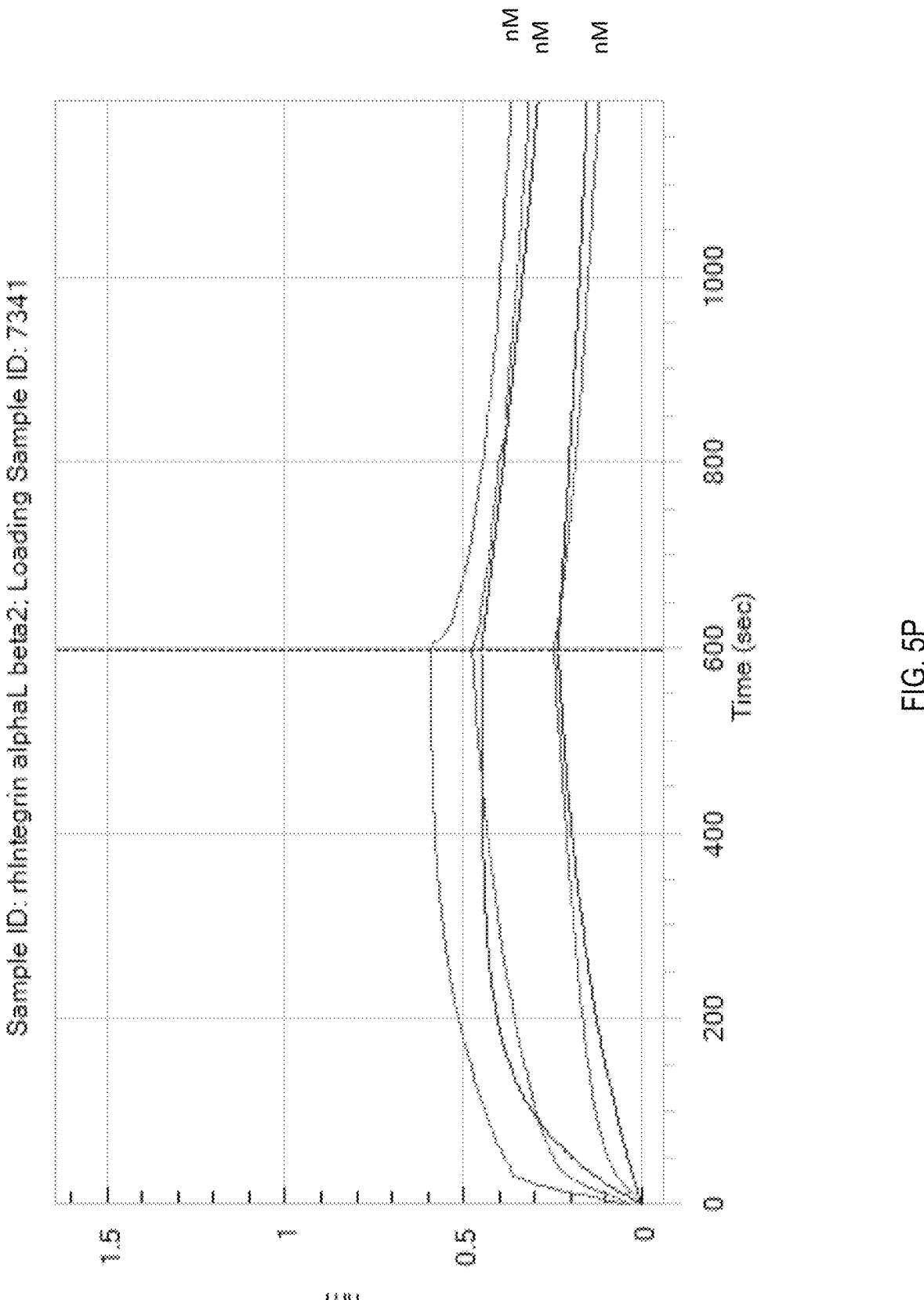
Figure 5Q:
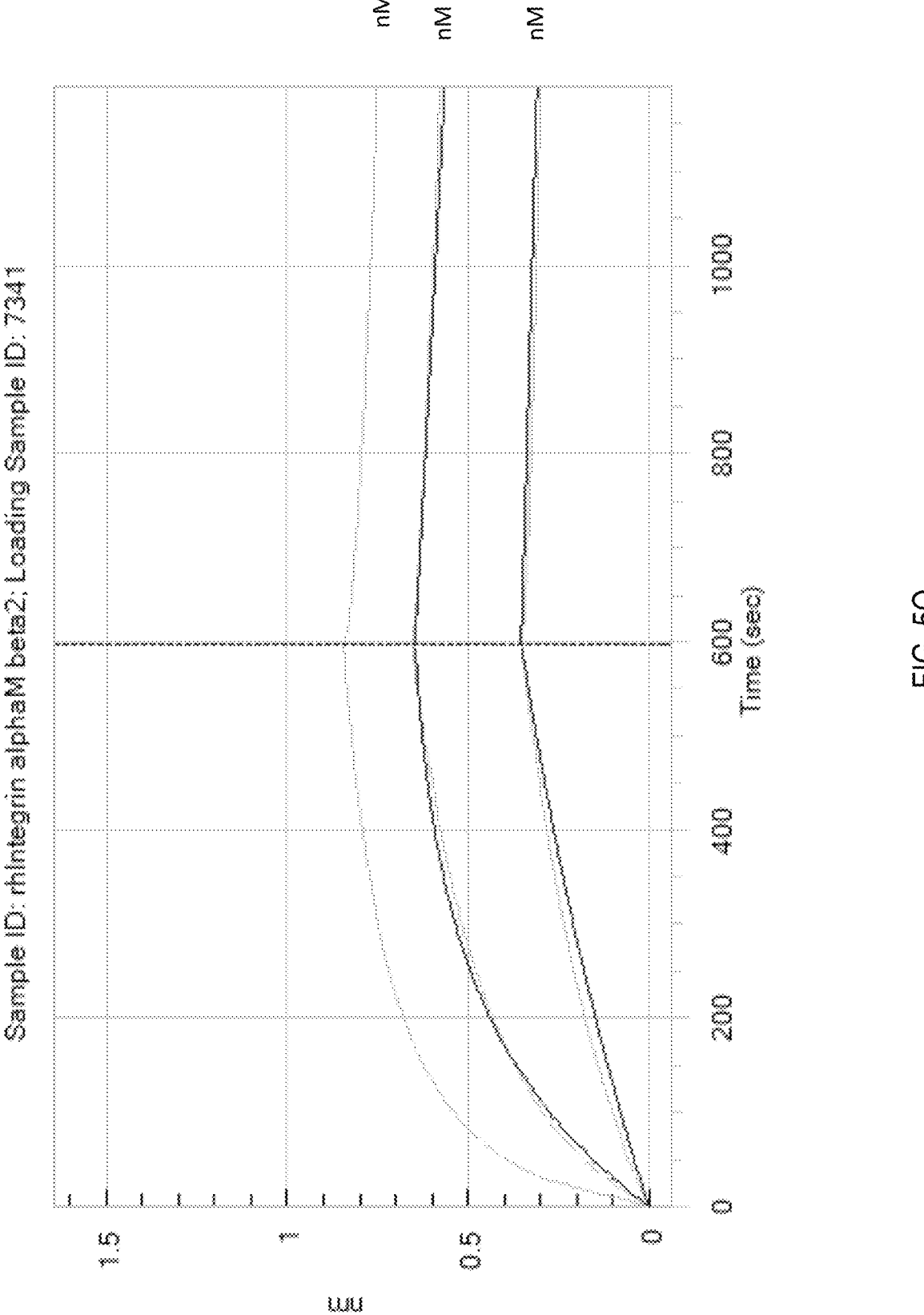
Figure 5R:
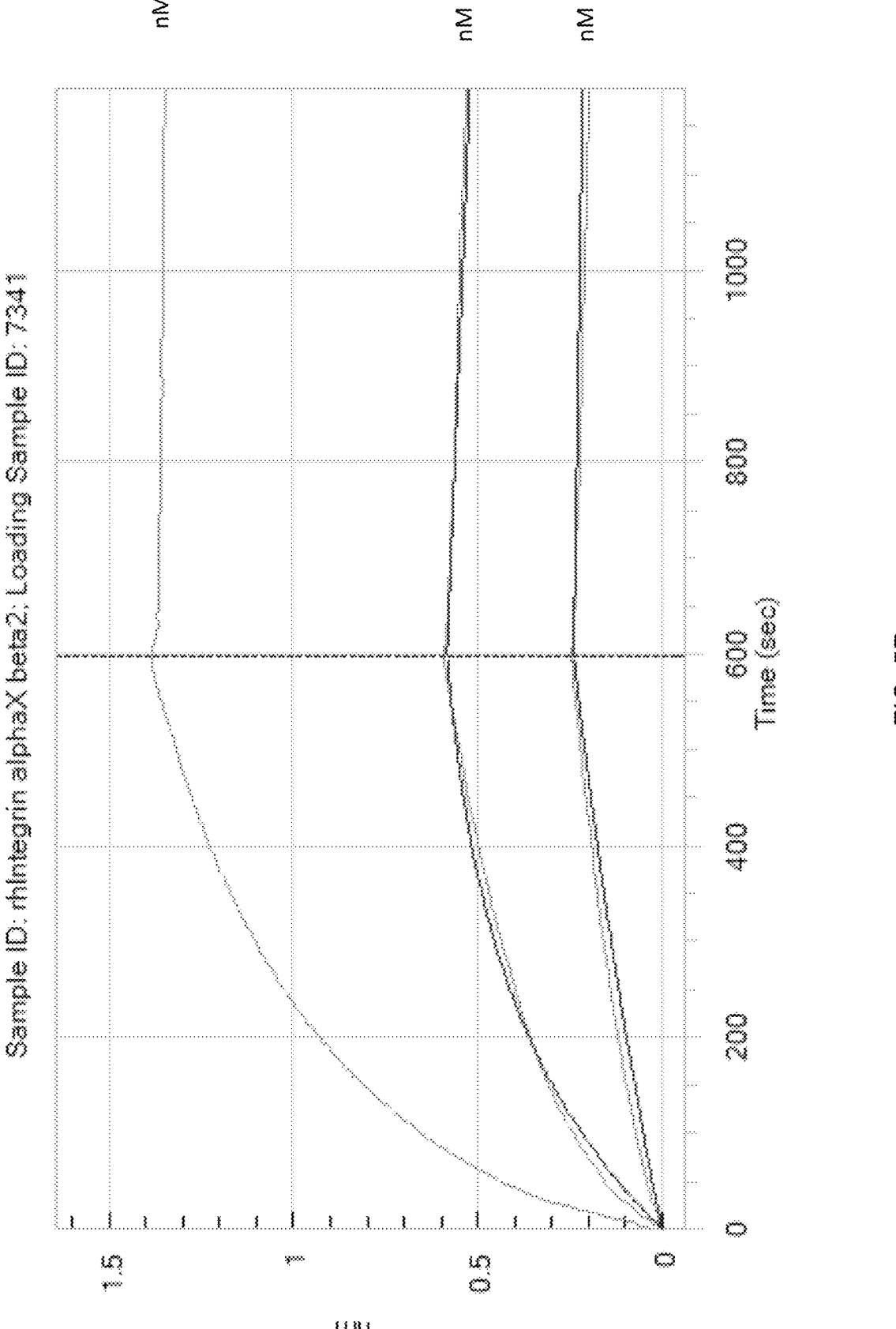

From the initial library diversity of ~$10^{10}$ binders, ten initial Fab hits shown in FIGS. 2A-2D and FIG. 3 were identified versus integrin-β2 recombinant heterodimer protein complexes. Seven of the Fab hits (#7055, #7056, #7057, #7060, #7061, #7062, #7063, #7064, #7065, #7341) were further validated using bio-layer interferometry (BLI) (see FIGS. 5A-5R and FIG. 6) and non-specific ELISA (see FIGS. 4A-4H) to have binding affinities to integrin beta-2 in the low-nM range and lack of binding to irrelevant proteins, respectively. These Fabs were cloned into a human IgG1 backbone and were purified following recombinant expression in mammalian cells, e.g., Expi93 human embryonic kidney cells or Chinese hamster ovary cells.

Antibody Production

Anti-integrin beta-2 antibodies were produced using the human Expi293 expression system (Thermofisher). Expi293 cells at 2 ml volume were transiently transfected with construct DNA using FectoPro transfection reagent (Polyplus Transfection, 101000014). Following a 5-day expression period, the antibodies were purified using rProteinA Sepharasoe (GE Healthcare) and stored in phosphate buffer (50 mM NaH2PO4, 75 mM Na2HPO4, 100 mM H3PO4, 154 mM NaCl).

Bio-Layer Interferometry (BLI) Binding Assays

The binding of human integrin beta-2 antibodies was tested against three different Integrin beta-2 complexes including integrin beta-2/integrin alpha-M (R and D 4047-AM), integrin beta-2/integrin alpha-X (R and D 5755-AX), and integrin beta-2/integrin alpha-L (R and D 3868-AV). To determine the binding kinetic parameters of the antibodies, BLI experiments were performed on an Octet HTX instrument (Sartorius) at 1000 rpm and 25° C. All proteins were diluted in an assay buffer (PBS, 1% BSA, 0.05% Tween 20). Test and control antibodies at a concentration of 2 µg/ml were first captured on AHQ biosensors to achieve the binding signals of 0.8-1.3 nm. Unoccupied Fc-binding sites on the antibody-coated sensors were subsequently quenched by 20 µg/mL of the Fc protein. After equilibration with the assay buffer, the biosensors were then dipped for 600 s into wells containing 5-fold serial dilution of Integrin-beta 2 complexes (association phase), followed by a transfer back into an assay buffer for additional 600 s (dissociation phase). Assay buffer alone served as a negative control. Binding response data were reference subtracted and were globally fitted with 1:1 binding model using ForteBio's Octet Systems software 9.0.

ELISA

The ELISA protocol to assess interactions of the antibodies with unrelated macromolecules was adapted from Meirsch et al. (J Vis Exp. 2015 Jan. 17; (95):51492). The tested antigens included Integrin AL/B2 (50 µg/mL, R&D systems 3868-AV-050), integrin AX/B2 (50 µg/mL, R&D systems 5755-AX-050), integrin AM/B2 (50 µg/mL, R&D systems 4047-AM-050), histidine tagged Sumo domain (100 µg/mL, recombinant), biotinylated Robo domain (100 µg/mL, recombinant), neutravidin (100 µg/mL, Pierce TPPI31000) or all other integrins proteins (50 µg/mL R&D systems). In addition, the binding of each antibody was also tested against empty wells (BSA only control) and wells containing goat anti-human Fc antibody (positive control, 1 µg/ml, Jackson 109-005-098). The antigens were coated at 30 µL per well in 384-well Maxisorp plates and incubated at 4° C. overnight. Plates were blocked with 0.5% bovine serum albumin (BSA) for 1 hour at room temperature and washed with PBS+0.05% Tween20. The Phage-Fab were added and allowed to bind for 60 min at room temperature. Plates were washed with PBS+0.05% Tween20 and binding was detected with anti-M13 HRP antibody (1:5000, Sinobiological 11973-MM05T-H) and developed with the TMB substrate (KPL (Mandel) KP-50-76-03). Statistical analysis All the statistical analysis were done using GraphPad Prism unless stated otherwise. The data have been represented as ±mean and p Value<0.05 were considered statistically significant.

Anti-Integrin Beta-2 Antibodies

Provided herein are anti-integrin beta-2 antibodies that can be used for diagnostic and therapeutic purposes.

In some embodiments, an anti-integrin beta-2 antibody of the present disclosure has a KD less than about 10 nM.

In some embodiments, an anti-integrin beta-2 binding domain of the present disclosure has at least one, at least two, or three CDRs of a variable domain sequence of SEQ ID NO:2 or SEQ ID NO:3. In some embodiments, an anti-integrin beta-2 binding domain of the present disclosure comprises an HCDR3 of SEQ ID NO:2 and an LCDR3 of SEQ ID NO:3. In some embodiments, an anti-integrin beta-2 binding domain comprises an HCDR1, HCDR2, and HCDR3 of SEQ ID NO:2 and LCDR1, LCDR2, and LCDR3 of SEQ ID NO:3.

In some embodiments, an anti-integrin beta-2 binding domain comprises an HCDR1, HCDR2, and HCDR3 of SEQ ID NO:2 in which one of the CDRs comprises a substitution relative to the corresponding CDR set forth in SEQ ID NO:2. In some embodiments, an anti-integrin beta-2 binding domain comprises an HCDR1, HCDR2, and HCDR3 of SEQ ID NO:2 in which two of the CDRs comprise a substitution relative to the corresponding CDRs set forth in SEQ ID NO:2. In some embodiments, an anti-integrin beta-2 binding domain comprises an HCDR1, HCDR2, and HCDR3 of SEQ ID NO:2 in which all three of the CDRs comprise a substitution relative to the corresponding CDR sequences set forth in SEQ ID NO:2.

In some embodiments, an anti-integrin beta-2 binding domain comprises an LCDR1, LCDR2, and LCDR3 of SEQ ID NO:3 in which one of the CDRs comprises a substitution relative to the corresponding CDR set forth in SEQ ID NO:3. In some embodiments, an anti-integrin beta-2 binding domain comprises an LCDR1, LCDR2, and LCDR3 of SEQ ID NO: 3 in which two of the CDRs comprise a substitution relative to the corresponding CDRs set forth in SEQ ID NO:3. In some embodiments, an anti-integrin beta-2 binding domain comprises an LCDR1, LCDR2, and LCDR3 of SEQ ID NO:3 in which all three of the CDRs comprise a substitution relative to the corresponding CDR sequences set forth in SEQ ID NO:3.

In some embodiments, an anti-integrin beta-2 binding domain of the present disclosure comprises a variable region having at least 70%, 75%, 85%, 90%, 91%, 92%, 93%, 94%, 95%, 96%, 97%, 98%, 99%, or 100% sequence identity to the amino acid sequence of a variable region sequence of SEQ ID NO:2 or SEQ ID NO:3. In some embodiments, the variable domain comprises substitutions, insertions, or deletions in the framework of a variable region as shown in SEQ ID NO:2 or SEQ ID NO:3. In some embodiments, an anti-integrin beta-2 binding domain of the present disclosure comprises a heavy chain variable region comprising the HCD1, HCDR2, and HCDR3 sequence of SEQ ID NO:2 and having at least 95% identity to SEQ ID NO:2; and a light chain variable region comprising the LCD1, LCDR2, LCDR3 sequences of SEQ ID NO:3 and having at least 95% identity to SEQ ID NO:3.

In some embodiments, an anti-integrin beta-2 binding domain of the present disclosure has at least one, at least two, or three CDRs of a variable domain sequence of SEQ ID NO:4 or SEQ ID NO:5. In some embodiments, an anti-integrin beta-2 binding domain of the present disclosure comprises an HCDR3 of SEQ ID NO:4 and an LCDR3 of SEQ ID NO:5. In some embodiments, an anti-integrin beta-2 binding domain comprises an HCDR1, HCDR2, and HCDR3 of SEQ ID NO:4 and LCDR1, LCDR2, and LCDR3 of SEQ ID NO:5.

In some embodiments, an anti-integrin beta-2 binding domain comprises an HCDR1, HCDR2, and HCDR3 of SEQ ID NO:4 in which one of the CDRs comprises a substitution relative to the corresponding CDR set forth in SEQ ID NO:4. In some embodiments, an anti-integrin beta-2 binding domain comprises an HCDR1, HCDR2, and HCDR3 of SEQ ID NO:4 in which two of the CDRs comprise a substitution relative to the corresponding CDRs set forth in SEQ ID NO:4. In some embodiments, an anti-integrin beta-2 binding domain comprises an HCDR1, HCDR2, and HCDR3 of SEQ ID NO:4 in which all three of the CDRs comprise a substitution relative to the corresponding CDR sequences set forth in SEQ ID NO:4.

In some embodiments, an anti-integrin beta-2 binding domain comprises an LCDR1, LCDR2, and LCDR3 of SEQ ID NO:5 in which one of the CDRs comprises a substitution relative to the corresponding CDR set forth in SEQ ID NO:5. In some embodiments, an anti-integrin beta-2 binding domain comprises an LCDR1, LCDR2, and LCDR3 of SEQ ID NO: 5 in which two of the CDRs comprise a substitution relative to the corresponding CDRs set forth in SEQ ID NO:5. In some embodiments, an anti-integrin beta-2 binding domain comprises an LCDR1, LCDR2, and LCDR3 of SEQ ID NO:5 in which all three of the CDRs comprise a substitution relative to the corresponding CDR sequences set forth in SEQ ID NO:5.

In some embodiments, an anti-integrin beta-2 binding domain of the present disclosure comprises a variable region having at least 70%, 75%, 85%, 90%, 91%, 92%, 93%, 94%, 95%, 96%, 97%, 98%, 99%, or 100% sequence identity to the amino acid sequence of a variable region sequence of SEQ ID NO:4 or SEQ ID NO:5. In some embodiments, the variable domain comprises substitutions, insertions, or deletions in the framework of a variable region as shown in SEQ ID NO:4 or SEQ ID NO:5. In some embodiments, an anti-integrin beta-2 binding domain of the present disclosure comprises a heavy chain variable region comprising the HCD1, HCDR2, and HCDR3 sequence of SEQ ID NO:4 and having at least 95% identity to SEQ ID NO:4; and a light chain variable region comprising the LCD1, LCDR2, LCDR3 sequences of SEQ ID NO:5 and having at least 95% identity to SEQ ID NO:5.

In some embodiments, an anti-integrin beta-2 binding domain of the present disclosure has at least one, at least two, or three CDRs of a variable domain sequence of SEQ ID NO:6 or SEQ ID NO:7. In some embodiments, an anti-integrin beta-2 binding domain of the present disclosure comprises an HCDR3 of SEQ ID NO:6 and an LCDR3 of SEQ ID NO:7. In some embodiments, an anti-integrin beta-2 binding domain comprises an HCDR1, HCDR2, and HCDR3 of SEQ ID NO:6 and LCDR1, LCDR2, and LCDR3 of SEQ ID NO:7.

In some embodiments, an anti-integrin beta-2 binding domain comprises an HCDR1, HCDR2, and HCDR3 of SEQ ID NO:6 in which one of the CDRs comprises a substitution relative to the corresponding CDR set forth in SEQ ID NO:6. In some embodiments, an anti-integrin beta-2 binding domain comprises an HCDR1, HCDR2, and HCDR3 of SEQ ID NO:6 in which two of the CDRs comprise a substitution relative to the corresponding CDRs set forth in SEQ ID NO:6. In some embodiments, an anti-integrin beta-2 binding domain comprises an HCDR1, HCDR2, and HCDR3 of SEQ ID NO:6 in which all three of the CDRs comprise a substitution relative to the corresponding CDR sequences set forth in SEQ ID NO:6.

In some embodiments, an anti-integrin beta-2 binding domain comprises an LCDR1, LCDR2, and LCDR3 of SEQ ID NO:7 in which one of the CDRs comprises a substitution relative to the corresponding CDR set forth in SEQ ID NO:7. In some embodiments, an anti-integrin beta-2 binding domain comprises an LCDR1, LCDR2, and LCDR3 of SEQ ID NO:7 in which two of the CDRs comprise a substitution relative to the corresponding CDRs set forth in SEQ ID NO:7. In some embodiments, an anti-integrin beta-2 binding domain comprises an LCDR1, LCDR2, and LCDR3 of SEQ ID NO:7 in which all three of the CDRs comprise a substitution relative to the corresponding CDR sequences set forth in SEQ ID NO:7.

In some embodiments, an anti-integrin beta-2 binding domain of the present disclosure comprises a variable region having at least 70%, 75%, 85%, 90%, 91%, 92%, 93%, 94%, 95%, 96%, 97%, 98%, 99%, or 100% sequence identity to the amino acid sequence of a variable region sequence of SEQ ID NO:6 or SEQ ID NO:7. In some embodiments, the variable domain comprises substitutions, insertions, or deletions in the framework of a variable region as shown in SEQ ID NO:6 or SEQ ID NO:7. In some embodiments, an anti-integrin beta-2 binding domain of the present disclosure comprises a heavy chain variable region comprising the HCD1, HCDR2, and HCDR3 sequence of SEQ ID NO:6 and having at least 95% identity to SEQ ID NO:6; and a light chain variable region comprising the LCD1, LCDR2, LCDR3 sequences of SEQ ID NO:7 and having at least 95% identity to SEQ ID NO:7.

In some embodiments, an anti-integrin beta-2 binding domain of the present disclosure has at least one, at least two, or three CDRs of a variable domain sequence of SEQ ID NO:8 or SEQ ID NO:9. In some embodiments, an anti-integrin beta-2 binding domain of the present disclosure comprises an HCDR3 of SEQ ID NO:8 and an LCDR3 of SEQ ID NO:9. In some embodiments, an anti-integrin beta-2 binding domain comprises an HCDR1, HCDR2, and HCDR3 of SEQ ID NO:8 and LCDR1, LCDR2, and LCDR3 of SEQ ID NO:9.

In some embodiments, an anti-integrin beta-2 binding domain comprises an HCDR1, HCDR2, and HCDR3 of SEQ ID NO:8 in which one of the CDRs comprises a substitution relative to the corresponding CDR set forth in SEQ ID NO:8. In some embodiments, an anti-integrin beta-2 binding domain comprises an HCDR1, HCDR2, and HCDR3 of SEQ ID NO:8 in which two of the CDRs comprise a substitution relative to the corresponding CDRs set forth in SEQ ID NO:8. In some embodiments, an anti-integrin beta-2 binding domain comprises an HCDR1, HCDR2, and HCDR3 of SEQ ID NO:8 in which all three of the CDRs comprise a substitution relative to the corresponding CDR sequences set forth in SEQ ID NO:8.

In some embodiments, an anti-integrin beta-2 binding domain comprises an LCDR1, LCDR2, and LCDR3 of SEQ ID NO:9 in which one of the CDRs comprises a substitution relative to the corresponding CDR set forth in SEQ ID NO:9. In some embodiments, an anti-integrin beta-2 binding domain comprises an LCDR1, LCDR2, and LCDR3 of SEQ ID NO:9 in which two of the CDRs comprise a substitution relative to the corresponding CDRs set forth in SEQ ID NO:9. In some embodiments, an anti-integrin beta-2 binding domain comprises an LCDR1, LCDR2, and LCDR3 of SEQ ID NO:9 in which all three of the CDRs comprise a substitution relative to the corresponding CDR sequences set forth in SEQ ID NO:9.

In some embodiments, an anti-integrin beta-2 binding domain of the present disclosure comprises a variable region having at least 70%, 75%, 85%, 90%, 91%, 92%, 93%, 94%, 95%, 96%, 97%, 98%, 99%, or 100% sequence identity to the amino acid sequence of a variable region sequence of SEQ ID NO:8 or SEQ ID NO:9. In some embodiments, the variable domain comprises substitutions, insertions, or deletions in the framework of a variable region as shown in SEQ ID NO:8 or SEQ ID NO:9. In some embodiments, an anti-integrin beta-2 binding domain of the present disclosure comprises a heavy chain variable region comprising the HCD1, HCDR2, and HCDR3 sequence of SEQ ID NO:8 and having at least 95% identity to SEQ ID NO:8; and a light chain variable region comprising the LCD1, LCDR2, LCDR3 sequences of SEQ ID NO:9 and having at least 95% identity to SEQ ID NO:9.

In some embodiments, an anti-integrin beta-2 binding domain of the present disclosure has at least one, at least two, or three CDRs of a variable domain sequence of SEQ ID NO:10 or SEQ ID NO:11. In some embodiments, an anti-integrin beta-2 binding domain of the present disclosure comprises an HCDR3 of SEQ ID NO:10 and an LCDR3 of SEQ ID NO:11. In some embodiments, an anti-integrin beta-2 binding domain comprises an HCDR1, HCDR2, and HCDR3 of SEQ ID NO:10 and LCDR1, LCDR2, and LCDR3 of SEQ ID NO:11.

In some embodiments, an anti-integrin beta-2 binding domain comprises an HCDR1, HCDR2, and HCDR3 of SEQ ID NO:10 in which one of the CDRs comprises a substitution relative to the corresponding CDR set forth in SEQ ID NO:10. In some embodiments, an anti-integrin beta-2 binding domain comprises an HCDR1, HCDR2, and HCDR3 of SEQ ID NO:10 in which two of the CDRs comprise a substitution relative to the corresponding CDRs set forth in SEQ ID NO:10. In some embodiments, an anti-integrin beta-2 binding domain comprises an HCDR1, HCDR2, and HCDR3 of SEQ ID NO:10 in which all three of the CDRs comprise a substitution relative to the corresponding CDR sequences set forth in SEQ ID NO:10.

In some embodiments, an anti-integrin beta-2 binding domain comprises an LCDR1, LCDR2, and LCDR3 of SEQ ID NO:11 in which one of the CDRs comprises a substitution relative to the corresponding CDR set forth in SEQ ID NO:11. In some embodiments, an anti-integrin beta-2 binding domain comprises an LCDR1, LCDR2, and LCDR3 of SEQ ID NO:11 in which two of the CDRs comprise a substitution relative to the corresponding CDRs set forth in SEQ ID NO:11. In some embodiments, an anti-integrin beta-2 binding domain comprises an LCDR1, LCDR2, and LCDR3 of SEQ ID NO:11 in which all three of the CDRs comprise a substitution relative to the corresponding CDR sequences set forth in SEQ ID NO:11.

In some embodiments, an anti-integrin beta-2 binding domain of the present disclosure comprises a variable region having at least 70%, 75%, 85%, 90%, 91%, 92%, 93%, 94%, 95%, 96%, 97%, 98%, 99%, or 100% sequence identity to the amino acid sequence of a variable region sequence of SEQ ID NO:10 or SEQ ID NO:11. In some embodiments, the variable domain comprises substitutions, insertions, or deletions in the framework of a variable region as shown in SEQ ID NO:10 or SEQ ID NO:11. In some embodiments, an anti-integrin beta-2 binding domain of the present disclosure comprises a heavy chain variable region comprising the HCD1, HCDR2, and HCDR3 sequence of SEQ ID NO:10 and having at least 95% identity to SEQ ID NO:10; and a light chain variable region comprising the LCD1, LCDR2, LCDR3 sequences of SEQ ID NO:11 and having at least 95% identity to SEQ ID NO:11.

In some embodiments, an anti-integrin beta-2 binding domain of the present disclosure has at least one, at least two, or three CDRs of a variable domain sequence of SEQ ID NO:12 or SEQ ID NO:13. In some embodiments, an anti-integrin beta-2 binding domain of the present disclosure comprises an HCDR3 of SEQ ID NO:12 and an LCDR3 of SEQ ID NO:13. In some embodiments, an anti-integrin beta-2 binding domain comprises an HCDR1, HCDR2, and HCDR3 of SEQ ID NO:12 and LCDR1, LCDR2, and LCDR3 of SEQ ID NO:13.

In some embodiments, an anti-integrin beta-2 binding domain comprises an HCDR1, HCDR2, and HCDR3 of SEQ ID NO:12 in which one of the CDRs comprises a substitution relative to the corresponding CDR set forth in SEQ ID NO:12. In some embodiments, an anti-integrin beta-2 binding domain comprises an HCDR1, HCDR2, and HCDR3 of SEQ ID NO:12 in which two of the CDRs comprise a substitution relative to the corresponding CDRs set forth in SEQ ID NO:12. In some embodiments, an anti-integrin beta-2 binding domain comprises an HCDR1, HCDR2, and HCDR3 of SEQ ID NO:12 in which all three of the CDRs comprise a substitution relative to the corresponding CDR sequences set forth in SEQ ID NO:12.

In some embodiments, an anti-integrin beta-2 binding domain comprises an LCDR1, LCDR2, and LCDR3 of SEQ ID NO:13 in which one of the CDRs comprises a substitution relative to the corresponding CDR set forth in SEQ ID NO:13. In some embodiments, an anti-integrin beta-2 binding domain comprises an LCDR1, LCDR2, and LCDR3 of SEQ ID NO:13 in which two of the CDRs comprise a substitution relative to the corresponding CDRs set forth in SEQ ID NO:13. In some embodiments, an anti-integrin beta-2 binding domain comprises an LCDR1, LCDR2, and LCDR3 of SEQ ID NO:13 in which all three of the CDRs comprise a substitution relative to the corresponding CDR sequences set forth in SEQ ID NO:13.

In some embodiments, an anti-integrin beta-2 binding domain of the present disclosure comprises a variable region having at least 70%, 75%, 85%, 90%, 91%, 92%, 93%, 94%, 95%, 96%, 97%, 98%, 99%, or 100% sequence identity to the amino acid sequence of a variable region sequence of SEQ ID NO:12 or SEQ ID NO:13. In some embodiments, the variable domain comprises substitutions, insertions, or deletions in the framework of a variable region as shown in SEQ ID NO:12 or SEQ ID NO:13. In some embodiments, an anti-integrin beta-2 binding domain of the present disclosure comprises a heavy chain variable region comprising the HCD1, HCDR2, and HCDR3 sequence of SEQ ID NO:12 and having at least 95% identity to SEQ ID NO:12; and a light chain variable region comprising the LCD1, LCDR2, LCDR3 sequences of SEQ ID NO:13 and having at least 95% identity to SEQ ID NO:13.

In some embodiments, an anti-integrin beta-2 binding domain of the present disclosure has at least one, at least two, or three CDRs of a variable domain sequence of SEQ ID NO:14 or SEQ ID NO:15. In some embodiments, an anti-integrin beta-2 binding domain of the present disclosure comprises an HCDR3 of SEQ ID NO:14 and an LCDR3 of SEQ ID NO:15. In some embodiments, an anti-integrin beta-2 binding domain comprises an HCDR1, HCDR2, and HCDR3 of SEQ ID NO:14 and LCDR1, LCDR2, and LCDR3 of SEQ ID NO:15.

In some embodiments, an anti-integrin beta-2 binding domain comprises an HCDR1, HCDR2, and HCDR3 of SEQ ID NO:14 in which one of the CDRs comprises a substitution relative to the corresponding CDR set forth in SEQ ID NO:14. In some embodiments, an anti-integrin beta-2 binding domain comprises an HCDR1, HCDR2, and HCDR3 of SEQ ID NO:14 in which two of the CDRs comprise a substitution relative to the corresponding CDRs set forth in SEQ ID NO:14. In some embodiments, an anti-integrin beta-2 binding domain comprises an HCDR1, HCDR2, and HCDR3 of SEQ ID NO:14 in which all three of the CDRs comprise a substitution relative to the corresponding CDR sequences set forth in SEQ ID NO:14.

In some embodiments, an anti-integrin beta-2 binding domain comprises an LCDR1, LCDR2, and LCDR3 of SEQ ID NO:15 in which one of the CDRs comprises a substitution relative to the corresponding CDR set forth in SEQ ID NO:15. In some embodiments, an anti-integrin beta-2 binding domain comprises an LCDR1, LCDR2, and LCDR3 of SEQ ID NO:15 in which two of the CDRs comprise a substitution relative to the corresponding CDRs set forth in SEQ ID NO:15. In some embodiments, an anti-integrin beta-2 binding domain comprises an LCDR1, LCDR2, and LCDR3 of SEQ ID NO:15 in which all three of the CDRs comprise a substitution relative to the corresponding CDR sequences set forth in SEQ ID NO:15.

In some embodiments, an anti-integrin beta-2 binding domain of the present disclosure comprises a variable region having at least 70%, 75%, 85%, 90%, 91%, 92%, 93%, 94%, 95%, 96%, 97%, 98%, 99%, or 100% sequence identity to the amino acid sequence of a variable region sequence of SEQ ID NO:14 or SEQ ID NO:15. In some embodiments, the variable domain comprises substitutions, insertions, or deletions in the framework of a variable region as shown in SEQ ID NO:14 or SEQ ID NO:15. In some embodiments, an anti-integrin beta-2 binding domain of the present disclosure comprises a heavy chain variable region comprising the HCD1, HCDR2, and HCDR3 sequence of SEQ ID NO:14 and having at least 95% identity to SEQ ID NO:14; and a light chain variable region comprising the LCD1, LCDR2, LCDR3 sequences of SEQ ID NO:15 and having at least 95% identity to SEQ ID NO:15.

Antibody Formats

An anti-integrin beta-2 antibody of the present disclosure may be incorporated into a bivalent antibody or a multivalent antibody that binds to the same, or a different, antigen. In some embodiments, an anti-Integrin beta-2 antibody of the present disclosure may be incorporated into a bispecific antibody or multispecific antibody that binds to the antigen at different epitopes, or that binds to different antigens. In some embodiments, such an antibody may comprise an Fc region. In some embodiments, an anti-integrin beta-2 antibody of the present disclosure may be present as an antigen binding domain of a larger molecule, e.g., present as an antigen binding domain of a chimeric antigen receptor or synthetic Notch receptor.

Nucleic Acids and Vectors Encoding CARS

Any method may be used to genetically modify an effector cell, such as a T-cell or NK cell to express a CAR comprising an anti-integrin beta-2 antibody of the present disclosure. Non-limiting examples of methods of genetically engineering immune cells include, but are not limited to, retrovirus- or lentivirus-mediated transduction. Other viral delivery systems include adenovirus, adeno-associated virus, herpes simplex viral vectors, pox viral vectors, alphavirus vectors, poliovirus vectors, and other positive and negative stranded RNA viruses, viroids, and virusoids, or portions thereof. Methods of transduction include direct co-culture of the cells with producer cells, e.g., by the method of Bregni, et al. (Blood 80: 1418-1422 (1992), or culturing with viral supernatant alone or concentrated vector stocks with or without appropriate growth factors and polycations, e.g., by the method of Xu, et al. Exp. Hemat. 22:223-230 (1994); and Hughes, et al. J. Clin. Invest. 89: 1817 (1992).

In some embodiments, genetic modification is performed using transposase-based systems for gene integration, CRISPR/Cas-mediated gene integration, TALENs or Zinc-finger nucleases integration techniques. For example, CRISPR/Cas-mediated gene integration may be employed to introduce a CAR or synthetic Notch receptor into immune effectors cells, which may then be selected and expanded for administration to a patient.

Antibody Conjugates

In a further aspect, an anti-integrin beta-2 antibody of the present disclosure may be conjugated or linked, either directly or indirectly, to therapeutic and/or imaging/detectable moieties. For example, in some embodiments, an antibody of the present disclosure, or an antigen binding region comprising an antibody of the present invention, may be conjugated to agents including, but not limited to, a detectable marker, a cytotoxic agent, an imaging agent, a therapeutic agent, or an oligonucleotide. Methods for conjugating or linking an antibody, or antigen binding regions comprising an antibody, to a desired molecule moiety are well known in the art. The moiety may be linked to the antibody covalently or by non-covalent linkages.

In some embodiments, an anti-Integrin beta-2 antibody of the present disclosure, or an antigen binding domain comprising an anti-integrin beta-2 antibody of the present disclosure, is conjugated to cytotoxic moiety or other moiety that inhibits cell proliferation.

In some embodiments, an anti-integrin beta-2 antibody of the present disclosure is conjugated to a cytotoxic agent including, but not limited to, e.g., ricin A chain, doxorubicin, daunorubicin, a maytansinoid, taxol, ethidium bromide, mitomycin, etoposide, tenoposide, vincristine, vinblastine, colchicine, dihydroxy anthracin dione, methotrexact, actino-mycin, a diphtheria toxin, extotoxin A from *Pseudomonas, Pseudomonas* exotoxin40, abrin, abrin A chain, modeccin A chain, alpha sarcin, gelonin, mitogellin, restrictocin, cobran venom factor, a ribonuclease, engineered Shiga toxin, phe-nomycin, enomycin, curicin, crotin, calicheamicin, *Saponaria officinalis* inhibitor, glucocorticoid, auristatin, auromycin, yttrium, bismuth, combrestatin, duocarmycins, dolastatin, cc1065, or a cisplatin. In some embodiments, the antibody may be linked to an agent such as an enzyme inhibitor, a proliferation inhibitor, a lytic agent, a DNA or RNA synthesis inhibitors, a membrane permeability modi-fier, a DNA metabolite, a dichloroethylsulfide derivative, a protein production inhibitor, a ribosome inhibitor, or an inducer of apoptosis.

In some embodiments, an anti-integrin beta-2 antibody of the present disclosure, or an antigen binding domain com-prising an anti-Integrin beta-2 antibody of the present dis-closure, may be linked to a radionuclide, an iron-related compound, a dye, a fluorescent agent, or an imaging agent. In some embodiments, an antibody may be linked to agents, such as, but not limited to, metals; metal chelators; lantha-nides; lanthanide chelators; radiometals; radiometal chela-tors; positron-emitting nuclei; microbubbles (for ultra-sound); liposomes; molecules microencapsulated in liposomes or nanosphere; monocrystalline iron oxide nano-compounds; magnetic resonance imaging contrast agents; light absorbing, reflecting and/or scattering agents; colloidal particles; fluorophores, such as near-infrared fluorophores.

While the above description provides examples of one or more antibodies and nucleic acids it will be appreciated that other compositions of matter may be within the scope of the claims as interpreted by one of skill in the art.

SEQUENCE LISTING

```
Sequence total quantity: 20
SEQ ID NO: 1              moltype = AA  length = 769
FEATURE                   Location/Qualifiers
source                    1..769
                          mol_type = protein
                          organism = Homo sapiens
SEQUENCE: 1
MLGLRPPLLA LVGLLSLGCV LSQECTKFKV SSCRECIESG PGCTWCQKLN FTGPGDPDSI   60
RCDTRPQLLM RGCAADDIMD PTSLAETQED HNGGQKQLSP QKVTLYLRPG QAAAFNVTFR   120
RAKGYPIDLY YLMDLSYSML DDLRNVKKLG GDLLRALNEI TESGRIGFGS FVDKTVLPFV   180
NTHPDKLRNP CPNKEKECQP PFAFRHVLKL TNNSNQFQTE VGKQLISGNL DAPEGGLDAM   240
MQVAACPEEI GWRNVTRLLV FATDDGFHFA GDGKLGAILT PNDGRCHLED NLYKRSNEFD   300
YPSVGQLAHK LAENNIQPIF AVTSRMVKTY EKLTEIIPKS AVGELSEDSS NVVQLIKNAY   360
NKLSSRVFLD HNALPDTLKV TYDSFCSNGV THRNQPRGDC DGVQINVPIT FQVKVTATEC   420
IQEQSFVIRA LGFTDIVTVQ VLPQCECRCR DQSRDRSLCH GKGFLECGIC RCDTGYIGKN   480
CECQTQGRSS QELEGSCRKD NNSIICSGLG DCVCGQCLCH TSDVPGKLIY GQYCECDTIN   540
CERYNGQVCG GPGRGLCFCG KCRCHPGFEG SACQCERTTE GCLNPRRVEC SGRGRCRCNV   600
CECHSGYQLP LCQECPGCPS PCGKYISCAE CLKFEKGPFG KNCSAACPGL QLSNNPVKGR   660
TCKERDSEGC WVAYTLEQQD GMDRYLIYVD ESRECVAGPN IAAIVGGTVA GIVLIGILLL   720
VIWKALIHLS DLREYRRFEK EKLKSQWNND NPLFKSATTT VMNPKFAES             769

SEQ ID NO: 2              moltype = AA  length = 444
FEATURE                   Location/Qualifiers
source                    1..444
                          mol_type = protein
                          organism = Synthetic construct
REGION                    29..34
                          note = HCDR1
REGION                    50..59
                          note = HCDR2
REGION                    99..101
                          note = HCDR3
SEQUENCE: 2
EVQLVESGGG LVQPGGSLRL SCAASGFTIS YYYMHWVRQA PGKGLEWVAS ISSSSGYTYY   60
ADSVKGRFTI SADTSKNTAY LQMNSLRAED TAVYYCARGA MDYWGQGTLV TVSSASTKGP   120
SVFPLAPSSK STSGGTAALG CLVKDYFPEP VTVSWNSGAL TSGVHTFPAV LQSSGLYSLS   180
SVVTVPSSSL GTQTYICNVN HKPSNTKVDK KVEPKSCDKT HTCPPCPAPE LLGGPSVFLF   240
PPKPKDTLMI SRTPEVTCVV VDVSHEDPEV KFNWYVDGVE VHNAKTKPRE EQYNSTYRVV   300
SVLTVLHQDW LNGKEYKCKV SNKALPAPIE KTISKAKGQP REPQVYTLPP SREEMTKNQV   360
SLTCLVKGFY PSDIAVEWES NGQPENNYKT TPPVLDSDGS FFLYSKLTVD KSRWQQGNVF   420
SCSVMHEALH NHYTQKSLSL SPGK                                       444

SEQ ID NO: 3              moltype = AA  length = 217
FEATURE                   Location/Qualifiers
source                    1..217
                          mol_type = protein
                          organism = Synthetic construct
REGION                    28..32
                          note = LCDR1
REGION                    50..56
                          note = LCDR1
REGION                    91..99
                          note = LCDR3
SEQUENCE: 3
DIQMTQSPSS LSASVGDRVT ITCRASQSVS SAVAWYQQKP GKAPKLLIYS ASSLYSGVPS   60
RFSGSRSGTD FTLTISSLQP EDFATYYCQQ FSSGSWAPIT FGQGTKVEIK RTVAAPSVFI   120
```

```
FPPSDEQLKS GTASVVCLLN NFYPREAKVQ WKVDNALQSG NSQESVTEQD SKDSTYSLSS   180
TLTLSKADYE KHKVYACEVT HQGLSSPVTK SFNRGEC                            217

SEQ ID NO: 4               moltype = AA  length = 450
FEATURE                    Location/Qualifiers
source                     1..450
                           mol_type = protein
                           organism = Synthetic construct
REGION                     29..34
                           note = HCDR1
REGION                     50..59
                           note = HCDR2
REGION                     99..107
                           note = HCDR3
SEQUENCE: 4
EVQLVESGGG LVQPGGSLRL SCAASGFTLS YSSMHWVRQA PGKGLEWVAY IYPSYGYTYY   60
ADSVKGRFTI SADTSKNTAY LQMNSLRAED TAVYYCARWS PGSGWAFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSREE   360
MTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                    450

SEQ ID NO: 5               moltype = AA  length = 214
FEATURE                    Location/Qualifiers
source                     1..214
                           mol_type = protein
                           organism = Synthetic construct
REGION                     28..32
                           note = LCDR1
REGION                     50..56
                           note = LCDR2
REGION                     91..96
                           note = LCDR3
SEQUENCE: 5
DIQMTQSPSS LSASVGDRVT ITCRASQSVS SAVAWYQQKP GKAPKLLIYS ASSLYSGVPS   60
RFSGSRSGTD FTLTISSLQP EDFATYYCQQ YHGSLITFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 6               moltype = AA  length = 449
FEATURE                    Location/Qualifiers
source                     1..449
                           mol_type = protein
                           organism = Synthetic construct
REGION                     29..34
                           note = HCDR1
REGION                     50..59
                           note = HCDR2
REGION                     99..106
                           note = HCDR3
SEQUENCE: 6
EVQLVESGGG LVQPGGSLRL SCAASGFTIS SYSIHWVRQA PGKGLEWVAS IYSYYGYTSY   60
ADSVKGRFTI SADTSKNTAY LQMNSLRAED TAVYYCARYW GYPYAMDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                     449

SEQ ID NO: 7               moltype = AA  length = 216
FEATURE                    Location/Qualifiers
source                     1..216
                           mol_type = protein
                           organism = Synthetic construct
REGION                     28..32
                           note = LCDR1
REGION                     50..56
                           note = LCDR2
REGION                     91..98
                           note = LCDR3
SEQUENCE: 7
DIQMTQSPSS LSASVGDRVT ITCRASQSVS SAVAWYQQKP GKAPKLLIYS ASSLYSGVPS   60
RFSGSRSGTD FTLTISSLQP EDFATYYCQQ YYYAASLFTF GQGTKVEIKR TVAAPSVFIF   120
PPSDEQLKSG TASVVCLLNN FYPREAKVQW KVDNALQSGN SQESVTEQDS KDSTYSLSST   180
LTLSKADYEK HKVYACEVTH QGLSSPVTKS FNRGEC                             216
```

-continued

```
SEQ ID NO: 8              moltype = AA  length = 451
FEATURE                   Location/Qualifiers
source                    1..451
                          mol_type = protein
                          organism = Synthetic construct
REGION                    29..34
                          note = HCDR1
REGION                    50..59
                          note = HCDR2
REGION                    99..108
                          note = HCDR3
SEQUENCE: 8
EVQLVESGGG LVQPGGSLRL SCAASGFTLS YSYMHWVRQA PGKGLEWVAS IYSYYSSTSY  60
ADSVKGRFTI SADTSKNTAY LQMNSLRAED TAVYYCARSY HYSYYAGLDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                451

SEQ ID NO: 9              moltype = AA  length = 213
FEATURE                   Location/Qualifiers
source                    1..213
                          mol_type = protein
                          organism = Synthetic construct
REGION                    28..32
                          note = LCDR1
REGION                    50..56
                          note = LCDR2
REGION                    91..95
                          note = LCDR3
SEQUENCE: 9
DIQMTQSPSS LSASVGDRVT ITCRASQSVS SAVAWYQQKP GKAPKLLIYS ASSLYSGVPS  60
RFSGSRSGTD FTLTISSLQP EDFATYYCQQ WYFLITFGQG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                              213

SEQ ID NO: 10             moltype = AA  length = 450
FEATURE                   Location/Qualifiers
source                    1..450
                          mol_type = protein
                          organism = Synthetic construct
REGION                    29..34
                          note = HCDR1
REGION                    50..59
                          note = HCDR2
REGION                    99..107
                          note = HCDR3
SEQUENCE: 10
EVQLVESGGG LVQPGGSLRL SCAASGFTLS YSSMHWVRQA PGKGLEWVAY IYSSSGYTYY  60
ADSVKGRFTI SADTSKNTAY LQMNSLRAED TAVYYCARWG WYAHAGMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 11             moltype = AA  length = 214
FEATURE                   Location/Qualifiers
source                    1..214
                          mol_type = protein
                          organism = Synthetic construct
REGION                    28..32
                          note = LCDR1
REGION                    50..56
                          note = LCDR2
REGION                    91..96
                          note = LCDR3
SEQUENCE: 11
DIQMTQSPSS LSASVGDRVT ITCRASQSVS SAVAWYQQKP GKAPKLLIYS ASSLYSGVPS  60
RFSGSRSGTD FTLTISSLQP EDFATYYCQQ WVHGLITFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 12             moltype = AA  length = 456
FEATURE                   Location/Qualifiers
source                    1..456
```

```
                               mol_type = protein
                               organism = Synthetic construct
REGION                         29..34
                               note = HCDR1
REGION                         50..59
                               note = HCDR2
REGION                         99..113
                               note = HCDR3
SEQUENCE: 12
EVQLVESGGG LVQPGGSLRL SCAASGFTLY YYSMHWVRQA PGKGLEWVAY IYPYYGYTSY  60
ADSVKGRFTI SADTSKNTAY LQMNSLRAED TAVYYCARTV RGSKKPYFSG WAMDYWGQGT  120
LVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKKVEPKSCD KTHTCPPCPA  240
PELLGGPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALPAP IEKTISKAKG QPREPQVYTL  360
PPSREEMTKN QVSLTCLVKG FYPSDIAVEW ESNGQPENNY KTTPPVLDSD GSFFLYSKLT  420
VDKSRWQQGN VFSCSVMHEA LHNHYTQKSL SLSPGK                            456

SEQ ID NO: 13                  moltype = AA   length = 216
FEATURE                        Location/Qualifiers
source                         1..216
                               mol_type = protein
                               organism = Synthetic construct
REGION                         28..32
                               note = LCDR1
REGION                         50..56
                               note = LCDR2
REGION                         91..98
                               note = LCDR3
SEQUENCE: 13
DIQMTQSPSS LSASVGDRVT ITCRASQSVS SAVAWYQQKP GKAPKLLIYS ASSLYSGVPS  60
RFSGSRSGTD FTLTISSLQP EDFATYYCQQ WGAWGPLITF GQGTKVEIKR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                            216

SEQ ID NO: 14                  moltype = AA   length = 444
FEATURE                        Location/Qualifiers
source                         1..444
                               mol_type = protein
                               organism = Synthetic construct
REGION                         29..34
                               note = HCDR1
REGION                         50..59
                               note = HCDR2
REGION                         99..101
                               note = HCDR3
SEQUENCE: 14
EVQLVESGGG LVQPGGSLRL SCAASGFTLS YYYMHWVRQA PGKGLEWVAS ISSYYGYTSY  60
ADSVKGRFTI SADTSKNTAY LQMNSLRAED TAVYYCARGA LDYWGQGTLV TVSSASTKGP  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK KVEPKSCDKT HTCPPCPAPE LLGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP SREEMTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGK                                         444

SEQ ID NO: 15                  moltype = AA   length = 216
FEATURE                        Location/Qualifiers
source                         1..216
                               mol_type = protein
                               organism = Synthetic construct
REGION                         28..32
                               note = LCDR1
REGION                         50..56
                               note = LCDR2
REGION                         91..98
                               note = LCDR3
SEQUENCE: 15
DIQMTQSPSS LSASVGDRVT ITCRASQSVS SAVAWYQQKP GKAPKLLIYS ASSLYSGVPS  60
RFSGSRSGTD FTLTISSLQP EDFATYYCQQ FYGGYSLITF GQGTKVEIKR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                            216

SEQ ID NO: 16                  moltype = AA   length = 6
FEATURE                        Location/Qualifiers
source                         1..6
                               mol_type = protein
                               organism = Synthetic construct
SEQUENCE: 16
```

-continued

```
ISYYYM                                                              6

SEQ ID NO: 17        moltype = AA   length = 10
FEATURE              Location/Qualifiers
source               1..10
                     mol_type = protein
                     organism = Synthetic construct
SEQUENCE: 17
SISSSSGYTY                                                          10

SEQ ID NO: 18        moltype = AA   length = 5
FEATURE              Location/Qualifiers
source               1..5
                     mol_type = protein
                     organism = Synthetic construct
SEQUENCE: 18
SVSSA                                                               5

SEQ ID NO: 19        moltype = AA   length = 7
FEATURE              Location/Qualifiers
source               1..7
                     mol_type = protein
                     organism = Synthetic construct
SEQUENCE: 19
SASSLYS                                                             7

SEQ ID NO: 20        moltype = AA   length = 9
FEATURE              Location/Qualifiers
source               1..9
                     mol_type = protein
                     organism = Synthetic construct
SEQUENCE: 20
FSSGSWAPI                                                           9
```

The invention claimed is:

1. An antibody that specifically binds to integrin beta-2, wherein the antibody comprises an integrin beta-2 binding domain comprising:
   a heavy chain variable region ($V_H$) comprising an HCDR1 sequence comprising amino acid sequence SEQ ID NO: 16, an HCDR2 sequence comprising amino acid sequence SEQ ID NO: 17; and an HCDR3 sequence comprising GAM; and
   a light chain variable region ($V_L$) comprising an LCDR1 sequence comprising amino acid sequence SEQ ID NO: 18, an LCDR2 sequence comprising amino acid sequence SEQ ID NO: 19; and an LCDR3 sequence comprising amino acid sequence SEQ ID NO: 20.

2. The antibody of claim 1, wherein the $V_H$ comprises an amino acid sequence having at least 95% identity to SEQ ID NO:2; and/or
   wherein the $V_L$ comprises an amino acid sequence having at least 95% identity to SEQ ID NO:3.

3. The antibody of claim 1, wherein the $V_H$ comprises amino acid sequence SEQ ID NO:2; and/or
   wherein the $V_L$ comprises amino acid sequence SEQ ID NO:3.

4. The antibody of claim 1, wherein the antibody is a single chain variable fragment (scFv).

5. The antibody of claim 4, wherein the $V_L$ is N-terminal to the $V_H$.

6. The antibody of claim 5, wherein the $V_H$ and the $V_L$ are separated by a flexible linker.

7. The antibody of claim 4, wherein the $V_H$ is N-terminal to the VL.

8. The antibody of claim 7, wherein the $V_H$ and the $V_L$ are separated by a flexible linker.

9. A bispecific or multispecific antibody comprising the antibody of claim 1.

10. A chimeric antigen receptor (CAR) comprising an antigen binding domain, wherein the antigen binding domain comprises the antibody of claim 1.

11. An immune effector cell comprising the CAR of claim 10.

12. The immune effector cell of claim 11, wherein the cell is a T-cell or an NK cell.

13. A polynucleotide encoding the antibody of claim 1.

14. A vector comprising the polynucleotide of claim 13.

15. An immune effector cell comprising the vector of claim 14.

16. A nucleic acid encoding an antibody $V_H$ and/or $V_L$, wherein the $V_H$ comprises an HCDR1 sequence comprising amino acid sequence SEQ ID NO: 16, an HCDR2 sequence comprising amino acid sequence SEQ ID NO: 17; and an HCDR3 sequence comprising GAM; and
   wherein the $V_L$ comprises an LCDR1 sequence comprising amino acid sequence SEQ ID NO: 18, an LCDR2 sequence comprising amino acid sequence SEQ ID NO: 19; and an LCDR3 sequence comprising amino acid sequence SEQ ID NO: 20.

17. The nucleic acid of claim 16, wherein the $V_H$ comprises an amino acid sequence having at least 95% identity to SEQ. ID NO: 2 and/or
   wherein the $V_L$ comprises an amino acid sequence having at least 95% identity to SEQ. ID NO: 3.

18. The nucleic acid of claim 16, wherein the $V_H$ comprises amino acid sequence SEQ ID NO:2; and/or
   wherein the $V_L$ comprises amino acid sequence SEQ ID NO: 3.

19. A vector comprising the nucleic acid of claim 16.

20. A host cell comprising the vector of claim 16.

* * * * *